(12) United States Patent
Gross et al.

(10) Patent No.: US 6,316,581 B1
(45) Date of Patent: Nov. 13, 2001

(54) BIORESORBABLE COPOLYMERS

(76) Inventors: Richard A. Gross, 16 Northern Pkwy. East, Plainview, NY (US) 11803; Rajesh Kumar, 353 50th St., Apartment Front, Brooklyn, NY (US) 11220

(*) Notice: Subject to any disclaimer, the term of this patent is extended or adjusted under 35 U.S.C. 154(b) by 0 days.

(21) Appl. No.: 09/780,213

(22) Filed: Feb. 9, 2001

(51) Int. Cl.[7] .................................................. C08G 64/00
(52) U.S. Cl. ........................................... 528/196; 528/198
(58) Field of Search ..................................... 528/196, 198

(56) References Cited

U.S. PATENT DOCUMENTS

| | | |
|---|---|---|
| 4,481,353 | 11/1984 | Nyilas . |
| 5,066,772 | 11/1991 | Tang . |
| 6,093,792 | 7/2000 | Gross . |

OTHER PUBLICATIONS

Ouchi et al., Makromol. Chem. 1989, 190 (1989).
Zhou et al., Macromolecules, 23, 3399 (1990).
Int'l Veld et al., Makromol. Chem. 1992, 193, 2713 (1992).
Barrera et al., Macromolecules, 28, 425 (1995).
Fietier et al., Polym. Bull. (Berlin) 24, 349 (1990).
Kawaguchi et al., Chem. Phar. Bull., 31, 1400, 4157 (1983).
Nishida et al., Chem. Lett. 1994, 3, 421 (1994).
Albertsson et al., Appl. Polym. Sci., 57 (1), 87 (1995).
Zhu et al., Macromolecules, 24, 1736 (1991).
Grijpma et al., Macromol. Chem. Phys., 195, 1633 (1994).
Buchholz, Mater. Sci., Mater. in Medicine, 4, 381 (1993).
Chen et al., Macromolecules, 30, 3470 (1997).
Tian et al., Macromolecules, 30, 406–409 (1997).
Vandenberg et al., Macromolecules, 32, 3613–3619 (1999).

*Primary Examiner*—Terressa M. Boykin
(74) *Attorney, Agent, or Firm*—Technoprop Colton LLC

(57) ABSTRACT

A bioresorbable copolymer composition comprising products of a reaction between a first comonomer comprising cyclic carbonates, lactones, lactides, lactams, thiolactones, functionalized cyclic carbonates and nonfunctionalized cyclic carbonates; and a second, functionalized, cyclic carbonate comonomer, wherein said second comonomer is a ring structure, wherein comprising a functional group.

61 Claims, 5 Drawing Sheets

BIORESORBABLE COPOLYMERS

BACKGROUND OF THE INVENTION

1. Technical Field

The present invention relates generally to the field of bioresorbable copolymers, and more specifically to bioresorbable copolymers that can be tailored for specific applications, including but not limited to bioresorbable medical materials and tissue engineering.

2. Prior Art

Water-soluble, biocompatible, bioresorbable copolymers and methods of preparation and use of such copolymers have been known and used in the prior art. For examples, bioresorbable material implants can be used for sutures, prosthetic devices, and drug release matrices and in some examples need not be removed subsequent to their use. Bioresorbable polymers having reactive pendant groups are of particular interest. The incorporation of repeat units containing vicinal diols into, for example, polylactide polymers, may impart unique properties to the prepared materials, which can facilitate a variety of potential applications.

Polylactide polymers (hereinafter [L]-poly(lactic acid) or [L]-PLA), which are bioresorbable polymers, have shown favorable biocompatibility and have gained wide acceptability for applications that require bioresorption in vivo. The [L]-poly(lactic acid) polymers have been used for many years, and have proved to be sterilizable and of low toxicity. [L]-PLA is produced from lactic acid, either by the direct condensation of lactic acid or via the ring opening polymerization of lactide. Polylactide also is one of the most practicable materials as a biodegradable material with respect to its synthesis from renewable resources, useful physical properties, cost, environmental biodegradability, biocompatibility, and bioresorbability.

The mechanical and physicochemical properties of [L]-PLA polymers are dependent on the polymer structure. The degradation rate of [L]-PLA based polymeric materials is a function of the amorphous/crystalline and hydrophilic/hydrophobic properties. The introduction of carbonate linkages into a polymer chain is an effective way to attain a spectrum of properties such as degradation behaviors and mechanical performance. Strategies to regulate these factors have involved copolymerizations of [L]-lactide with [D]-lactide, glycolide, ethylene oxide, ε-caprolactone, and monomers that upon ring-opening provide amino acid repeat units.

The prior art discloses an array of examples that employ strategies to tailor PLA physico-mechanical properties and hydrolytic degradability by blending PLA with other polymers and copolymerizing [L]-lactide with other monomers. For example, U.S. Pat. No. 5066772 to Tang et al. discloses a bioresorbable copolymer that includes both carbonate repeating units and hydroxycarboxylic acid repeating esters units. Other examples of such copolymers are PLA polyesters with pendant carboxyl and amine functional groups such as those from malic acid and [L]-serine ester repeat units that have been disclosed by Ouchi et al., *Makromol. Chem.* 1989, 190 (1989) and, Zhou et al. *Macromolecules*, 23, 3399 (1990). Additionally, PLA polydepsipeptides with carboxyl, amino or thiol groups have also been published. In't Veld et al., *Makromol. Chem.* 1992, 193, 2713 (1992).

The prior art discloses examples in which biopolymer chains are decorated to facilitate the attachment of various bioactive substances. Such decoration is recognized as being important in tissue engineering applications. Barrera et al., *Macromolecules*, 28, 425 (1995); Fietier et al., *Polym. Bull. (Berlin)* 24, 349 (1990). Barrera et al., *Macromolecules*, 28, 425 (1995), prepared a copolymer of poly(lactic acid-co-lysine) with RGD attached to the lysine residues at a surface concentration of 310 fmol/cm$^2$. The RGD peptide functions to promote cell adhesion. However, the use of this copolymer has been restricted because the molecular weight of poly(lactic acid-co-lysine) copolymers decreased significantly relative to [L]-LA homopolymerization, even with low 3-[N-(carbonyl-benzoxy)-L-lysyl]-6-L-methyl-2,5-morpholinedione co-monomer feed ratios.

The prior art discloses a number of aliphatic polycarbonates or their copolymers that may be degradable. Examples cited in the literature include poly(ethylene carbonate) and poly(TMC). Kawaguchi et al., *Chem. Pharm. Bull.*, 31, 1400, 4157 (1983); Nishida et al., *Chem. Lett.* 1994, 3, 421 (1994); Albertsson et al., *Appl. Polym. Sci.*, 57 (1), 87 (1995), Zhu et al., *Macromolecules*, 24, 1736 (1991). Other degradable carbonate containing copolymers include TMC/LA, TMC/CL, and TMC or 2,2-dimethyl-TMC/butyrolactone. Grijpma et al., *Macromol. Chem. Phys.*, 195, 1633 (1994), Buchholz, *Mater. Sci., Mater. In Medicine*, 4, 381 (1993).

The prior art discloses the introduction of functional entities into homo- and copolymers that are linked by carbonate or ester/carbonate bonds. For example, high molecular weight polycarbonates containing vinyl pendant groups were prepared by the homopolymerization of 4,4-cyclohexene-1,3-trimethylene carbonate. Chen et al., *Macromolecules*, 30, 3470 (1997). The vinyl pendant groups were partially or completely converted into epoxides by oxidation with chloroperoxybenzoic acid. Chen et al., *Macromolecules*, 30, 3470 (1997).

The prior art discloses a number of examples of bioresorbable copolymers comprising monomers with carboxylic acid. U.S. Pat. No. 6093792 to Gross discloses high molecular weight bioresorbable copolymers constructed to be useful for specific applications in the biomedical arts and includes a new cyclic carbonate monomer, 1,2-O-isopropylidene-D-xylofuranose-3,5-cyclic carbonate (IPXTC), and copolymers containing the new monomers, wherein the ketal groups were hydrolyzed to give copolymers of lactic acid and xylofuranose that have hydroxyl side groups. In addition, U.S. Pat. No. 5066772 to Tang et al. discloses a copolymer containing repeating units of carbonate and units of hydroxycarboxylic acid repeating esters that are bioresorbable. U.S. Pat. No. 4481353 to Nyilas et al. discloses a bioresorbable copolymer with polyesters composed of a Kreb Cycle intermediate and an alpha-hydroxy carboxylic acid from the group consisting of glycolic acid, L-lactic acid, and D-lactic acid.

The prior art discloses examples of polymers gaining a functional hydroxyl group after deprotection of the ketal group. For example, Tian et al. prepared 1,4,8-trioxaspiro[4,6]-9-undecanonone (or 5-ethylene ketal-caprolactone). Tian, et al., *Macromolecules*, 30, 406–409 (1997). The removal of the ketal protecting groups of repeat units from 5-ethylene ketal-caprolactone gave hydroxyl side chains. Vandanberg and co-workers prepared 2,2-dimethyl-5,5-bis(hydroxymethyl)-1,3-dioxane, which is the cyclic carbonate from the monoketal diol of pentaerythritol. Vandenberg, E. J. and Tian, D., *Macromolecules*, 32, 3613–3619 (1999). Deprotection led to a water-insoluble but water-swollen product.

The present reference and its incorporated references disclose copolymers and their constituents that are distinct from the prior art in ways including but not limited to structure and reactivity. One important distinction from the prior art is that the present invention comprises bioresorbable copolymers that contain 1,2-O-isopropylidene-3-benzyloxy-glucofuranose-4,4'-cyclic carbonate (IPGTC) and other bioresorbable comonomers such as lactide. In addition, this polymer is significantly more tailorable than the prior art polymers because of a novel built-in control allowing one, two or three free hydroxyl side groups in IPGTC repeats. This tailorable system is expected to have great value in the development of new bioresorbable medical materials. There is a need in the field of the present invention for the ability to strategically place functional groups that can facilitate covalent pro-drug attachment, cell targeting, control cell differentiation, and other biological and physical functions. Notwithstanding the prior art, there exists a need for a distinct bioresorbable material that is nontoxic, able to be thermally processed, and sufficiently flexible in structure to meet the needs for bioresorbable polymers.

BRIEF SUMMARY OF THE INVENTION

The present invention is directed to bioresorbable copolymers. Bioresorbable copolymers with low-level toxicity are attractive materials for uses such as but not limited to implantables in living organisms, drug carrier systems and tissue engineering. The present invention provides a novel monomer of 1,2-isopropylidene- 3-benzyloxy-glucofuranose-4,4'-cyclic carbonate (hereinafter IPGTC), a novel copolymer comprising IPGTC and [L]-lactide repeat units, and various methods of constructing the comonomer and the copolymer.

The present invention is related to novel, thermally processible, highly tailorable bioresorbable copolymers. The novel copolymers can be produced by polymerizing the novel comonomer of IPGTC with comonomers such as but not limited to [L]-LA, [D]-LA, racemic-LA, meso-LA, glycolide, trimethylene carbonate (TMC), δ-valerolactone, dioxanone, ethylene oxide, c-caprolactone using ring-opening polymerization reactions. The copolymerization of [L]-LA and IPGTC is shown below:

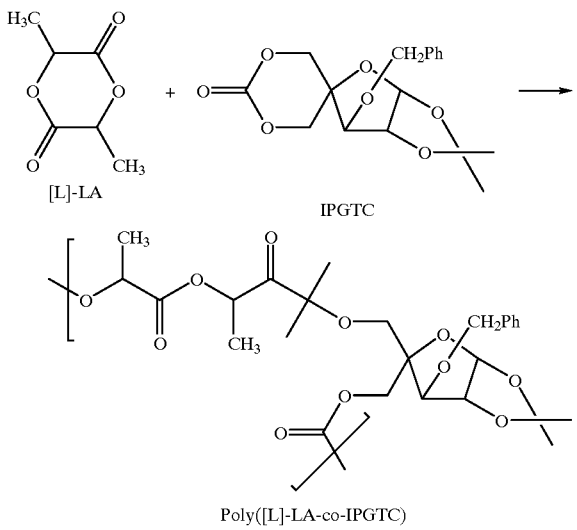

Poly([L]-LA-co-IPGTC)

The novel copolymers of the present invention are highly functionalized by the inclusion of a variety of pendant groups and, as a result, the copolymers are highly adaptable and able to interact with many useful and biologically active substrates. The copolymers comprise a mono-, di-, or tri-hydroxy pendant system. These three side group options arise due to the built-in ability of IPGTC repeat units to be selectively deprotected without significant loss of molecular weight in the copolymer. Depending on the feed ratios and reaction conditions, the copolymers can have a random or defined pattern of repeat units and can have ester and/or carbonate bonds between the comonomers. The formed copolymers can be further functionalized upon modification by the removal of the ketal protecting group via deketalization and removal of the benzyl group via debenzylation.

An additional aspect of the present invention is a method of preparing functionalized bioresorbable copolymers by: (1) preparing the comonomer IPGTC; (2) polymerizing the comonomer IPGTC with L-LA; and (3) introducing additional functionality in the polymer via deketalization and/or debenzylation.

The copolymerization reaction can be conducted under an array of conditions and with a variety of reagents. The polymerization can proceed with or without a catalyst. The ratios of reagents can be varied to produce the desired characteristics within the copolymer. The use of deketalization and debenzylation can produce a copolymer of desired functionality and composition.

It is an object of the present invention to provide a copolymer that may be used as a bioresorbable material.

It is another object of the present invention to provide a copolymer that offers a unique system having 1, 2, or 3 available hydroxyl groups for each functional repeat unit, which results from the ability to selectively remove benzyl, ketal or combination of benzyl and ketal groups without substantial loss in the molecular weight of the copolymer chain, and allows for an unprecedented ability to fine-tune and manipulate the biological and physical properties of the biomaterial copolymer.

It is another object of the present invention to provide a copolymer, wherein the selective removal of the benzyl and ketal groups offers some unique system to decorate the copolymer with different bioactive molecules that are located in well-defined locations relative to each other.

It is another object of the present invention to provide a high molecular weight, functionalized, bioresorbable copolymer that is suitable to be processed thermally using known techniques to result in a material that can be used for an array of uses such as but not limited to medical devices, tissue engineering and drug delivery or may be processed into films, sheets, foams, fibers or solid objects of any shape.

It is another object of the present invention to provide a copolymer that can become or is active with or without being metabolized.

It is another object of the present invention to provide a copolymer that can be incorporated, chemically or physically, into another material.

It is another object of the present invention to provide a copolymer that decomposes into essentially nontoxic components.

It is another object of the present invention to provide a copolymer that can be converted into a graft polymer.

These objects, and other objects, features and advantages of the present invention, will become more apparent to those of ordinary skill in the art when the following detailed description of the preferred embodiments is read in conjunction with the appended examples and figures, in which like reference numerals represent like components throughout the figures.

DETAILED DESCRIPTION OF THE PREFERRED EMBODIMENTS

Figure 1:
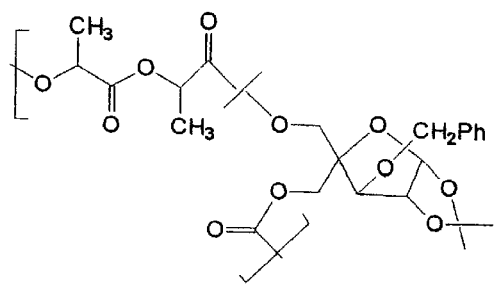
FIG. 1 displays a generalized depiction of an IPGTC comonomer linked to another monomer in a copolymer.

In this specification, various terms are defined as follows.

A "bioresorbable" compound is one that can be degraded to lower molecular weight compounds that may or may not be eliminated from a living organism. Such lower molecular weight compounds also may be metabolized by organisms.

A "biodegradable" compound is one that can be acted upon biochemically by living cells or organisms, or parts of these systems, or reagents commonly found in such cells, organisms, or systems, including water, and broken down into lower molecular weight products. The organism may play an active or passive role in such actions.

"Chemical reactions" can include the formation or dissociation of ionic, covalent, or noncovalent structures through known means. "Bonds," "bonding," or "linkages" are ionic, covalent, or noncovalent bonds of all types. Physical reactions can include changes in environmental conditions such as pH, ionic strength, and temperature.

A "polymer" can be a homopolymer and/or copolymer, or combinations thereof. If the stereochemical configuration of lactide is not defined by [L]- or [D]-, then the lactide monomer is presumed to be without optical activity or to be a racemic mixture.

"Nontoxic" generally refers to substances that, upon ingestion, inhalation, or absorption through the skin by a human or animal, do not cause, either acutely or chronically, damage to living tissue, impairment of the central nervous system, severe illness, or death. The term "nontoxic" also can refer to compounds, the hydrolysate or metabolites of which can be incorporated innocuously and without harm to the surrounding environment. The opposite of "nontoxic" is defined as "toxic."

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition, the materials, methods, and examples are illustrative only and not intended to be limiting.

The preferred embodiment of the present invention is directed to bioresorbable copolymers for an array of uses such as but not limited to medical devices, tissue engineering, drug delivery and other areas where such resorbable copolymers may be useful or processed into films, sheets, foams, fiber, or solid objects of any shape. Specifically, the preferred embodiment includes a novel comonomer of 1,2-O-isopropylidene-3-benzyloxy-glucofuranose-4-cyclic carbonate (IPGTC), copolymers comprising the comonomer comprising lactones and cyclic carbonates (hereinafter Comonomer I) and comonomer IPGTC (hereinafter Comonomer II or the IPGTC comonomer), and methods to synthesize the IPGTC comonomer and polymers comprising IPGTC. Copolymers comprising IPGTC, after removal of the benzyl, ketal or both of these moieties of its side groups, can give chains that contain [L]-Lactic acid and IPGTC repeat units with functional pendant groups. The chain of the copolymer is expected to biodegrade forming nontoxic metabolites.

Figure 2:
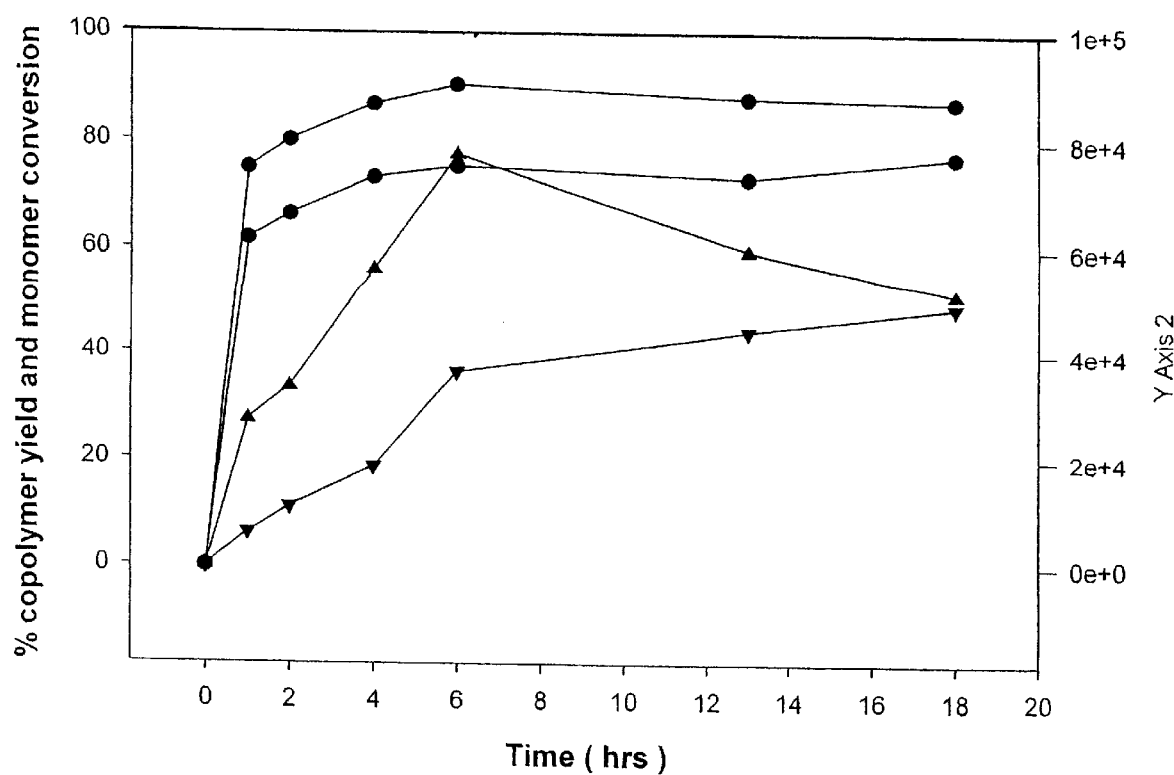
FIG. 2 displays the relationship between the reaction time, reaction temperature, monomer conversion, copolymer yield, and molecular weight for the reaction leading to the production of a bioresorbable material of the present invention.
Figure 3:
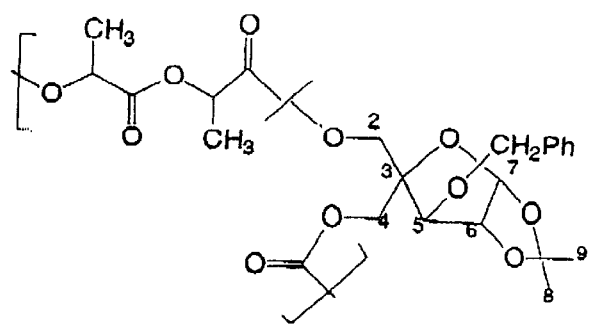
FIG. 3 displays the $^1$H NMR spectrum of poly ([L]-LA-co-15 mol % IPGTC) synthesized by Sn (Oct)$_2$ at 130° C.
Figure 3:
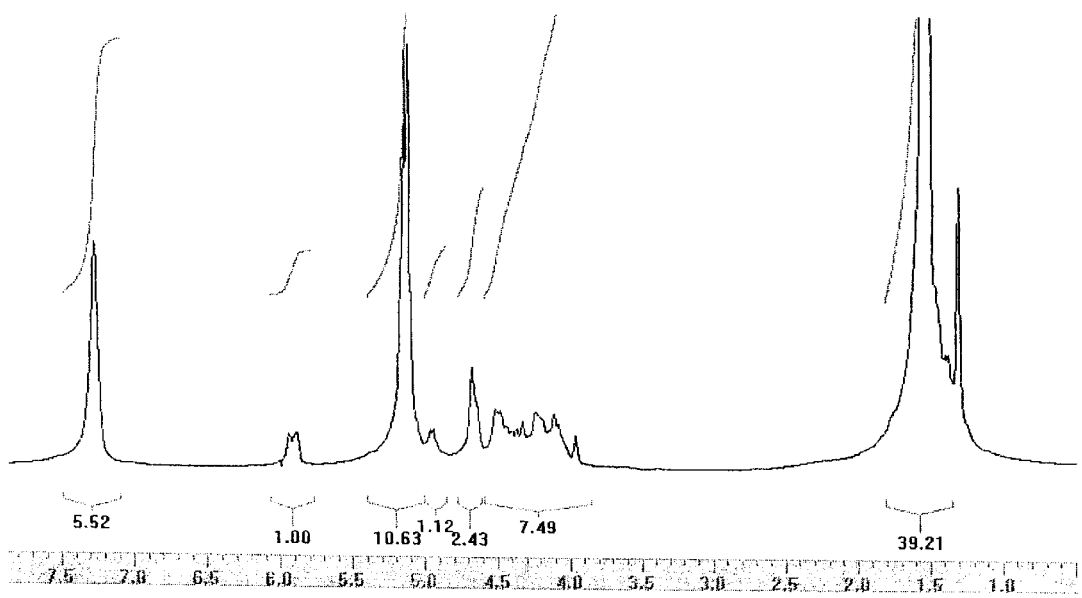
Figure 4:
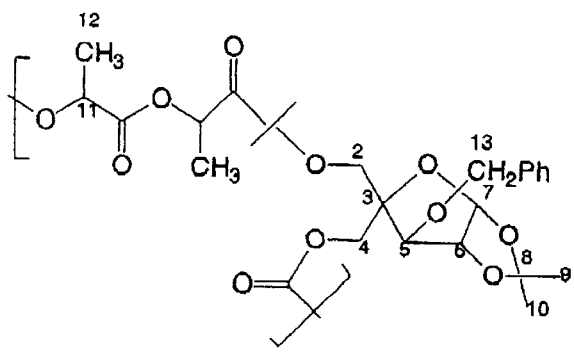
FIG. 4 displays the $^{13}$C-NMR spectrum of poly ([L]-LA-co-15 mol % IPGTC).
Figure 4:
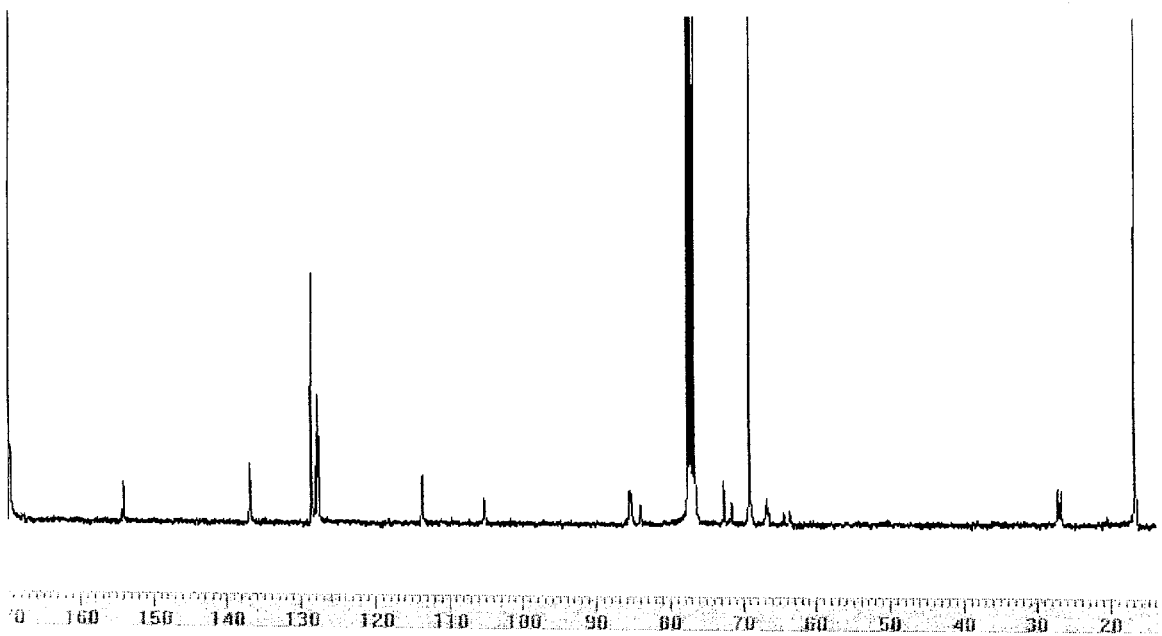

FIG. 1 displays a generalized depiction of an IPGTC comonomer linked to another monomer in a copolymer. FIG. 2 displays the relationship between the reaction time, reaction temperature, monomer conversion, copolymer yield, and molecular weight for the reaction leading to the production of one of the bioresorbable materials of the present invention. Preferably, the [D]-glucofuranose of the IPGTC comonomer provides a route to decorate PLA-based copolymers with monohydroxyl and vicinal diol pendant groups. FIG. 3 provides a $^1$H NMR spectrum of poly([L]-LA-co-15 mol % IPGTC) and illustrates the functional groups of the IPGTC copolymer. FIG. 4, which provides $^{13}$C NMR information on the microstructure of the [L]-LA/IPGTC copolymers, illustrates the considerable complexity of the copolymer with its functionalized pendant groups.

The preferred embodiment provides bioresorbable copolymers with pendant functional groups, or mixtures of such pendant groups in single copolymers or mixtures of copolymers. The pendant groups of copolymers of this invention are functional and can provide sites to bind biologically active molecules through electrostatic bonds, hydrogen bonds, van der Waals bonds, covalent bonds, and or hydrophobic bonds. The novel comonomer and/or copolymer of the present invention can be used in practice to prepare a flexible array of copolymers. The comonomers and/or copolymers include homopolymers, copolymers, or physical combinations of homopolymers and/or copolymers. The present invention includes higher order copolymers comprising other mixtures of comonomers with IPGTC and allows for various functional groups that can allow a person of ordinary skill in the art to control the binding of the polymer characteristics to substrate molecules, i.e., the specific capabilities of different molecules for covalent and/or non-covalent interactions.

The comonomer and/or copolymer in the preferred embodiment can be arranged in a pattern that is random, block, alternating, graft, network, and blended copolymers, or mixtures thereof. The monomer and/or copolymer of the present invention can be incorporated chemically or physically into other materials. Further, the copolymers and/or comonomers in the preferred embodiment can be biodegradable and bioresorbable.

For illustrative purposes, the block arrangement described above can have repeating block units such as AB, ABA, BAB, ABAB, ABABA, BABAB, and the like, where each A block and each B block contains the same or substantially the same number of recurring units. Alternatively, the various A and B blocks contained in the block copolymers can have more than one type or types of recurring monomeric units, or each block can contain the same or different types of recurring units, but have a differing number of recurring units in each block. With respect to the recurring blocks of As and Bs, each of them can also be the same or different. The polymer chains of this invention must consist in part of IPGTC units. However, the only other requirement is that the other comonomers used are bioresorbable and degrade to non-toxic products. The copolymers of this invention also can be of the type known as graft polymers. The IPGTC units in the graft copolymers can be in the main chain and/or in the graft units.

The percent of the IPGTC comonomer in the composition of IPGTC containing copolymers can vary greatly depending on the conditions employed. Under some conditions, the polymer can be composed of 100 percent IPGTC. Under other conditions, the percent can be as low as 0.001 percent. The person of ordinary skill in the art will be able to select the conditions and percent of IPGTC in the composition of the Comonomer I/IPGTC copolymer without deviating from the sprit of the preferred embodiment. An embodiment can entail a composition of IPGTC that will allow for biodegradation and sufficient incorporation of hydroxy pendant groups along the chain.

The weight average molecular weight (Mw) of the Comonomer I/IPGTC copolymer can range between 1000 to 1,000,000 grams per mole. The preferred range will depend on the application of the copolymer. A person of ordinary skill in the art can vary the reaction parameters without undue experimentation to achieve a preferred average molecular number.

The molecular weight distributions are characterized by a polydispersity value ($M_w/M_n$). $M_n$ is the number average molecular weight of a polymer and is defined by the weight of a given sample of polymer divided by the number of molecules within that sample. $M_w$ is the weight average molecular weight and is defined by the summation of the product of the molecular weight of the species, squared, and the number of molecules of the species, divided by the summation of the product of the molecular weight of the species and the number of molecules of the species. Copolymers useful for the purposes of the new compositions have polydispersity values of between 1.0 and 10.0, and more preferably between 1.02 and 2.3. A person of ordinary skill in the art can vary the reaction parameters without undue experimentation to achieve a preferred polydispersity.

A person of ordinary skill in the art also will recognize that the Comonomer I/IPGTC copolymer blocks can deviate from random compositions, can have a range of molecular weights, and can be combinations of relatively short chains or individual species which confer specifically desired properties while retaining the required characteristics of the copolymer. The lengths of IPGTC/Comonomer I oligomers referred to herein may vary from single units to many units depending on reaction conditions. A person of ordinary skill in the art has the knowledge to control the reaction conditions to form oligomers and block copolymers of IPGTC and Comonomer I.

Bioresorbable polymers having pendant functional groups are of particular interest, since they are capable of covalent and non-covalent binding to bioactive molecules. By variation of the pendant functional groups, previously unattainable variations in hydrophobicity, macroscopic physical properties, degradability, and chain binding properties can be achieved. Further functionalization of the copolymer is also possible as described below.

The IPGTC copolymers can be used in diverse concentrations to prepare a variety of different polymer blend compositions. Useful blend compositions can be made that consist of 100 percent of the new IPGTC copolymers, or they can include low amounts of the new IPGTC copolymers, with the balance of the blend composition being a functionalized or nonfunctionalized bioresorbable copolymer.

The hydroxyl groups of the Comonomer 1/IPGTC copolymer, which arise selectively upon de-protection steps, can impart unique properties and can allow for a variety of potential applications. For example, bioactive moieties can be covalently bound to the hydroxyl groups of the new copolymers. Alternatively, linear and cross-linked hydroxyl-containing polyesters can permit the formation of strong hydrogen bonding interactions with organic and inorganic species. Thus, contacting new copolymers that contain hydroxyl groups with molecules that can form hydrogen-bonding interactions with these groups such as proteins, carbohydrates, and peptides can result in compositions in which the molecules are encapsulated or substantially encapsulated by the new copolymers. Introduction of these compositions into organisms by a variety of means results in time-release of those molecules through biodegradation and bioresorption. Hydroxyl groups could interact with or bind to bioactive molecules, with similar implications for encapsulation and time-release.

Another characteristic imparted by deprotected hydroxyl groups on the Comonomer I/IPGTC copolymers is to enhance the hydrolytic degradability of the corresponding polymeric material. The hydrophilic character of hydroxyl-containing copolymers is greatly increased, and water molecules associated with the inner or bulk material of such copolymers can assist hydrolytic degradation via the nucleophilic attack of water at ester linkages. A person of ordinary skill in the art can without undue experimentation determine copolymer compositions and the amount of hydroxyl groups needed for a degradation time.

Cross-linking of hydroxyl-containing copolymers can take place through any of the well-known methods used for crosslinking materials such as cellulose. These methods include but are not limited to treatment with formaldehyde or other aldehydes, epoxides or diepoxides, or certain non-toxic sulfones, such as bis (2-hydroxyethyl) sulfone. Diisocyanates or dianhydrides can also be used to cross-link hydroxyl-containing copolymers.

Figure 6:
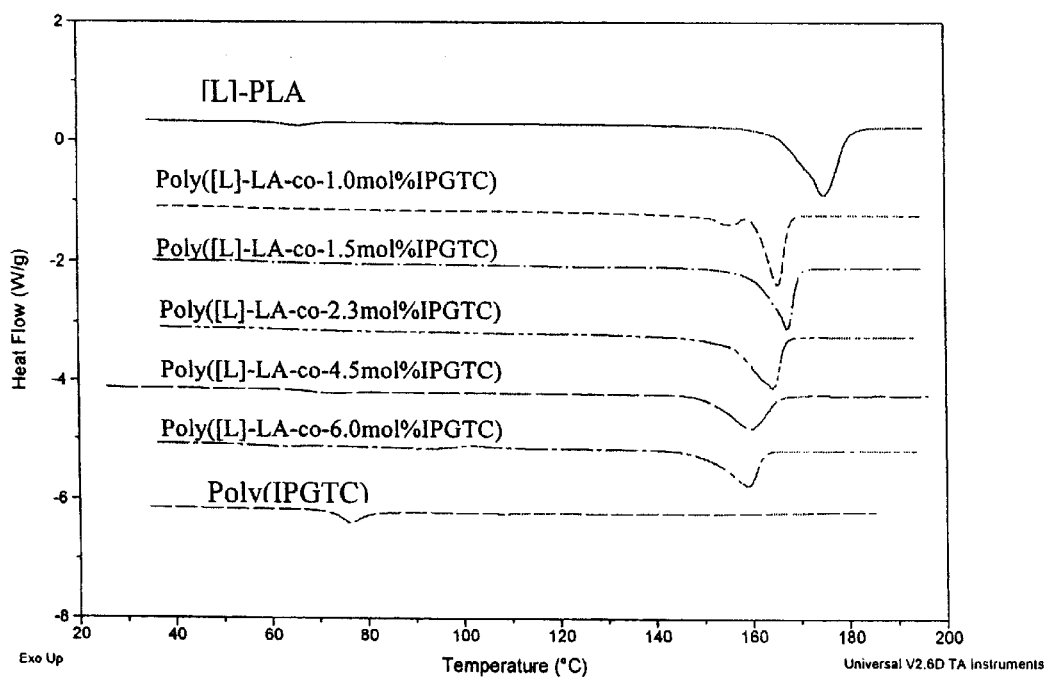
FIG. 6 displays the first heating DSC scans of [L]-LA/IPGTC copolymers at variable composition and shows a decrease in the melting point from 174° Celsius (pure PLA) to 156° C.
Figure 7A:
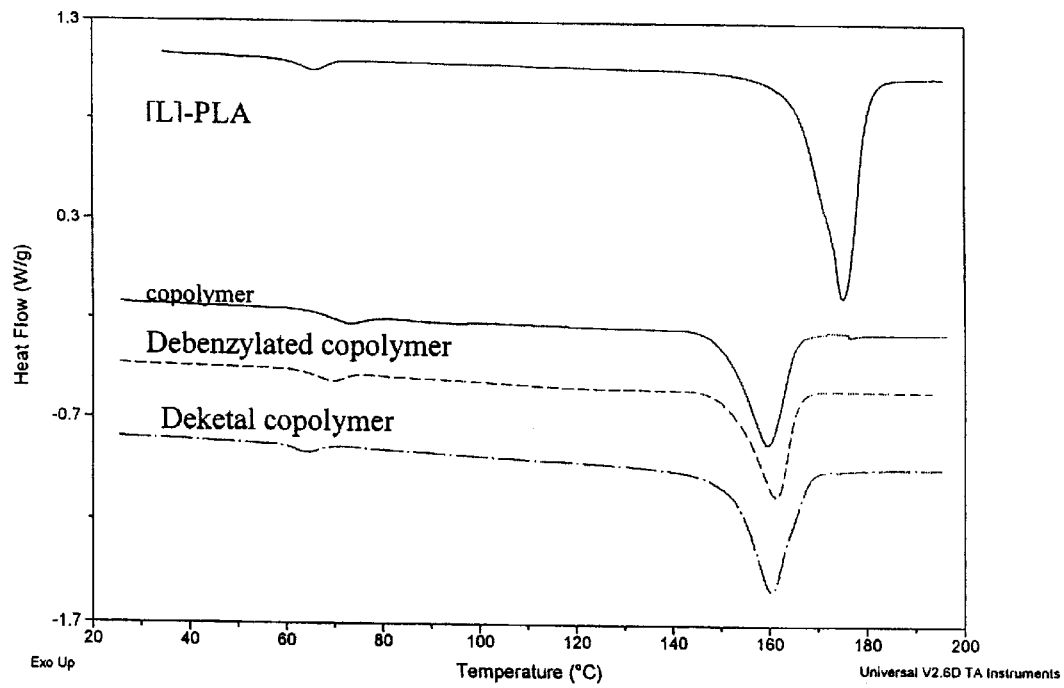
FIG. 7A displays the first heating DSC scans of [L]-LA/IPGTC copolymers before and after benzyl and ketal protecting groups were removed.

Thermal gravimetric analyses of the Comonomer I/IPGTC copolymer in the preferred embodiment and such copolymer after deprotection suggest a high degree of thermal stability. This permits the IPGTC copolymers to be stable at temperatures above 200° C. This also allows polymerization at high temperatures (>140° C.). In addition, the thermal stability of IPGTC copolymers will allow for their processing in the melt. FIG. 6 displays the first heating DSC scans of [L]-LA/IPGTC copolymers at variable composition and shows a decrease in the melting point ($T_m$) from 174° C. (pure PLA) to 156° C. FIG. 7A displays the first heating DSC and FIG. 7B displays the second heating scan of the following polymers: [L]-PLA, poly([L]-LA-co-4.5 mol % IPGTC), debenzylated poly([L]-LA-co-4.5 mol % IPGTC), and deketal poly ([L]-LA-co-4.5 mol % IPGTC). Both figures indicate that the incorporation of IPGTC is correlated with higher thermal stability.

An additional aspect of the preferred embodiment includes Comonomer I/IPGTC polymers, wherein Comonomer I can be but is not limited to [L]-lactide. The copolymer IPGTC repeat units then are reacted so as to selectively free one hydroxyl, two hydroxyls, or all three hydroxyls. The formed deprotected hydroxyl groups then can be reacted with another monomer or mixtures of monomers including but not limited to lactones, unfunctionalized cyclic carbonates, functionalized cyclic carbonates (e.g. IPGTC), and chain segments such as polyethyleneglycol. Such graft copolymerizations may require a catalyst that would be evident to those of ordinary skill in the art. The resulting graft copolymers will be bioresorbable. These graft copolymers can be used to link by covalent, ionic, hydrogen-bonding, or hydrophobic association, a pharmaceutically active substance. Examples of classes of pharmaceutically active substances include but are not limited to proteins, oligopeptides, oligosaccharides, and anticancer agents.

These graft copolymers can be used for the design of improved interfacial agents for bioresorbable blends. Graft polymers may be derived for use in tissue engineering applications by the attachment of biologically active molecules to the functional groups to promote favorable cell-polymer interactions. Further, graft polymers are useful as scaffolds to support cell growth in tissue engineering. In these embodiments, polymers or copolymers grafted onto the new functionalized bioresorbable copolymers can be other functionalized or unfunctionalized bioresorbable copolymers from polymerizations of lactone-, lactam-, thiolactone-, or amino acid N-carboxy anhydride-based copolymers.

An additional aspect of the preferred embodiment includes the graft ring-opening polymerization from deprotected hydroxyl functional groups of IPGTC with monomers, which can contain amino acid side chains, such as but not limited to amino acid N-carboxyanhydrides (NCA). Further, the NCA graft ring-opening polymerizations can be initiated by chain functional groups within the pores of foams that contain the new functional copolymers. In this way, the pore structure of new foams is adjustable for optimal interactions with cell colonies.

Preferred Comonomers

The preferred embodiment of the present category of new copolymers comprises two main repeated components designated as Comonomer I (being a monomer from a group comprising cyclic carbonates, lactones, lactides, lactams, thiolactones, functionalized cyclic carbonates and nonfunctionalized cyclic carbonates or the like) and Comonomer II (being IPGTC).

1. Comonomer I

The first component of the preferred embodiment, Comonomer I, can be selected from the following groups comprising cyclic carbonates, lactones, lactides, lactams, thiolactones, functionalized cyclic carbonates and nonfunctionalized cyclic carbonates such as but not limited to [L]-LA, trimethylene carbonate (TMC), ε-caprolactone, ethylene oxide, glycolide, δ-valerolactoctone, dioxanone, and other structures which can undergo ring opening reactions. The copolymers can include repeating units of Comonomer I, which is preferably from [L]-LA. Generally, the copolymer can comprise more than about 25 weight percent repeating units derived from lactide, and in some examples, greater than about 50 weight percent. In some lactide-containing embodiments, the polymer is prepared by polymerization of a composition including lactide in which greater than about 50% by weight of the lactide is optically active and less than 50% is optically inactive, i.e., racemic [D,L]-lactide and meso [D,L]-lactide. It is recognized that the optical activity of the lactide monomers within a polymer can be varied to fine-tune the copolymer properties.

Generally, linear [L]-LA containing polymers are formed from ring-opening polymerization of the cyclic dimeric ester of lactic acid, i.e., lactide. While the mechanism for the polymerization of Comonomer I or IPGTC is not fully understood, the polymerization mechanism appears to include chain propagation in a linear fashion. The polymerization is initiated by a nucleophilic group. The nucleophillic group can be an OH group and can be from water, an alcohol, lactic acid, or other materials. The nucleophillic group reacts with one of the carbonyl groups of the cyclic dimer to open the lactide ring. As a consequence of the ring-opening event, a new nucleophilic group, i.e. an —OH group, is generated at the terminal end of the polymer backbone. The newly generated —OH group can react with another lactide molecule that can result in another ring-opening event. The final molecular weight of the polymer, the length of the chains, and the molecular weight will depend on the number of monomers polymerized and the number of nucleophilic initiator sites. A person of ordinary skill in the art will recognize that there are other theories that may be used to construct copolymers containing IPGTC with Comonomer I or the like.

2. Comonomer II

The preferred embodiment comprises a second comonomer, IPGTC, which can occur in repeating units throughout the IPGTC/Comonomer I (group) copolymer. IPGTC is a novel 6-member cyclic carbonate with a 5-member ring interrupted with 1 oxygen with benzyl ether and ketal protected saccharide, and can be copolymerized with Comonomer I.

The preferred structure of the novel monomer 1,2-O-isopropylidene-3-benzyloxy-glucofuranose-4,4'-cyclic carbonate (IPGTC) was prepared having two sets of hydroxyl groups, a ketal protected diol and a benzyl ether protected hydroxyl on the 5-member sugar ring. The preferred IPGTC has the following structure:

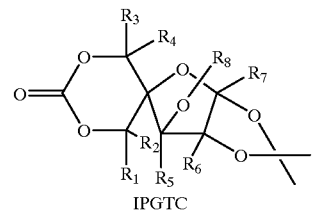

IPGTC

Preferably, as shown above in the structure of IPGTC, the R-groups 1–8 of IPGTC are flexible and can be selected from the group consisting of but not limited to hydrogen, alkanes, alkenes, alkynes, amine, amide, aromatic rings, alcohols, ethers, carboxylic acids, esters, and nitriles. Most preferably, R-groups 1–7 are hydrogen.

The R-group 8 of IPGTC can be selected from the group consisting of but not limited to benzyl, acetonide, DMT, benzonide, benzoyl, acetyl, tetrahydropyran, acrylate, methyl methacrylate, courmaryol, and nucleic acids. Most preferably, R-group 8 is a benzyl moiety.

It also has been observed that irrespective of the temperature or time period of copolymer synthesis the incorporation of IPGTC into the copolymer was less than that used in the monomer feed. This result suggests that the reactivity of [L]-LA is substantially greater than that of the IPGTC.

Method For Producing A Copolymer

Another aspect of the preferred embodiment is a method for producing the Comonomer I/IPGTC copolymer. The preferred method comprises 3 basic schemes. First, the novel monomer IPGTC is synthesized. Second, Comonomer I is copolymerized with the monomer IPGTC to create a Comonomer I/IPGTC copolymer. Third, the copolymer can be tailored for functionality by deketalization and/or debenzylation.

1. Synthesis of Comonomer II (IPGTC)

Preferably, the synthetic reaction is conducted in the absence of impurities that contain active agents or catalysts. The preferred method is conducted in an inert and anhydrous environment.

The preferred method of preparing Comonomer II or IPGTC is commenced by preparation of cyclic carbonate of 4-C-hydroxymethyl-1,2-O-(1-methylethylidene)-3-O-(phenylmethyl)-α-D-pentofuranose (HPP). To prepare HPP, ethyl chloroformate and 1,2-O-isopropylidene-D-xylofuranose were dissolved in tetrahydrofuran (THF). Triethylamine was added drop wise to a mixture of HPP and ethyl chloroformate dissolved in tetrahydrofuran (THF) at low temperatures over time. The reaction can be performed at but is not limited to temperatures between approximately 30° C. and 40° C. Further, the reaction can be monitored by techniques such as but not limited to thin layer chromatography. After completion, the precipitated triethylamine hydrochloride can be filtered out, and the filtrate can be concentrated under reduced pressure and recrystallized from THF and diethylether. The following shows the basic reaction and type of reagents.

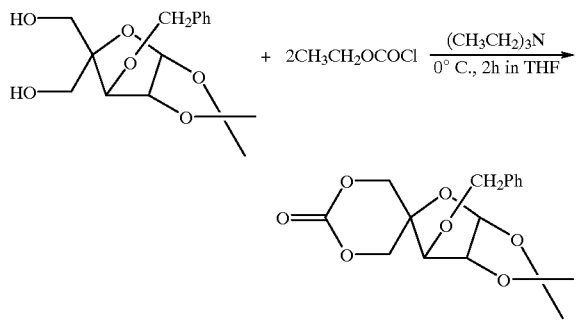

1

IPGTC can be synthesized in yields ≧65% by a one pot reaction in tetrahydrofuran (THF) at 0° C. starting with 1,2-O-isopropylidene-3-benzyloxy-4-(bishydroxymethyl) glucofuranose (see above Equation 1). The structure and purity of IPGTC was confirmed by FTIR, $^1$H NMR, $^{13}$C NMR and melting point analysis. It is understood that yield, purity, structure, or other characteristics of IPGTC will depend on reaction conditions.

The preferred embodiment includes the incorporation of the above repeating comonomer IPGTC in an amount ranging from 0.001 to 100.0 mole percent. The preferable amount of incorporation of IPGTC is between 1 to 10 mole percent.

A person of ordinary skill in the art will recognize that IPGTC can be synthesized using permutations of this method or can be synthesized using other techniques, reagents, solvents, or reaction conditions.

2. Method of Copolymerization of Comonomer I and II

The preferred embodiment provides a method of copolymerizing Comonomer I and Comonomer II (IPGTC) by a ring opening polymerization reaction, as shown below in Equation 2. As used hereinafter, the term [L]-LA is used to designate a representative structure within Comonomer I type. The IPGTC can be obtained via the method above and the [L]-LA or the like can be obtained from a commercial chemical source.

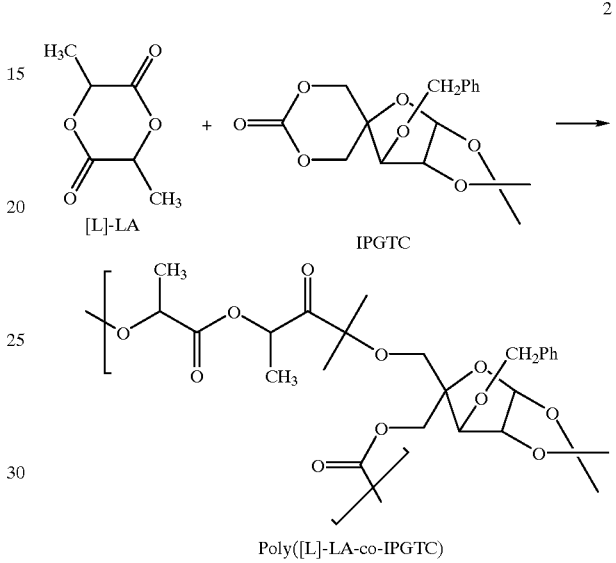

2

Preferably, the polymerization technique is performed in the absence of impurities, which can contain active agents or unwanted catalysts. Such impurities can cause a decrease in product yield and molecular weight. The preferred method is conducted in an inert and anhydrous environment. Methods to ensure a impurity free environment can include but are not limited to treating the reaction vessel walls with trimethylsilyl chloride, washing it with methanol, drying in an oven, and flame drying while purging with dried argon.

The preferred catalysts for the ring opening copolymerization of [L]-LA with IPGTC of the present invention is the organometallic catalyst $Sn(Oct)_2$. The use of $Sn(Oct)_2$ is widely accepted as a catalyst for the ring opening polymerization of [L]-LA and other medical grade bioresorbable polyesters. Other organometal catalysts that can be used for this copolymerization include but are not limited to various derivatives of $ZnEt_2$-$H_2O$, $AlEt_3$, $Al(isobutyl)_3$, $Al(O-secbutyl)_3$, $Al(O-isopropyl)_3$, $La(OR)_3$, and $Y(OR)_3$, wherein R is ethyl, isobutyl, secbutyl, or isopropoxyl. Analysis by GPC of copolymer product prepared by $Sn(Oct)_2$ catalysis showed unimodal distributions and the polydispersities ($M_w/M_n$) were in the range 1.6–2.3. The catalyst $Sn(Oct)_2$ for the polymerization reaction was prepared in dry toluene.

The amount of catalyst in the preferred embodiment is the normal amount used in these types of polymerization reactions and is known by those of ordinary skill in this field. Prior to use, a solution in dry toluene can be prepared.

The comonomers and the catalyst solution can be transferred into the preferred reaction environment, such as an ampule, under an inert argon atmosphere to undergo bulk polymerization. The ampule can be degassed by several vacuum-purge cycles or the like that also remove solvent introduced in the catalyst solution. The ampule then can be sealed under argon and placed in an oil bath for a predetermined reaction time.

At the end of the reaction period, the copolymer product can be purified using known techniques. One such method includes dissolving the contents of the ampule in chloroform. The purified copolymer can be precipitated from the chloroform solution by adding the reaction solution to methanol. The precipitate, a more purified polymer, can be washed with several portions of methanol, and dried in a vacuum oven.

The preferred time for the reaction of IPGTC and [L]-LA conducted at 130° C. is between 4 and 8 hours, and preferably approximately 6 hours. The polymerization reaction will occur during times greater than and less than 6 hours, and the preferred time for a desired result can be determined without undue experimentation. The plot of copolymer yield, $M_n$ and monomer conversion versus reaction time are displayed in FIG. 2 and illustrates that 6 hours is preferable because of the copolymer molecular weight and yield. A rapid increase was observed for the first hours leading up to the yield in the preferred time. However, at reaction times greater than 6 hours, the product was of lower molecular weight and lower yields. It will be recognized by a person of ordinary skill in the art that reaction time depends upon and varies with an array of conditions. Specifically, a person of ordinary skill in the art will understand that the reaction can be halted at any time to achieve a desired characteristic in the polymer.

The preferred feed ratio of Comonomer I to Comonomer II, [L]-LA and IPGTC respectively, is 91:9, which give suitable yield and molecular weight of the IPGTC copolymer. The feed ratio of monomers appears to change the yield of the polymer. The polymerization can occur in various feed ratios. It was observed that increased copolymer IPGTC content resulted in products with lower molecular weight and in low isolated yields. A decrease in copolymer percent-yield and Mn values were observed by increasing the IPGTC content in the monomer feed ratio. It has been observed that by decreasing the feed ratio of [L]-LA:IPGTC from 91:9 to 64:36, the IPGTC molar content in the copolymers increased from 4 to 14 mol percent. The feed ratio can be altered to achieve a desired molecular weight and/or yield.

The preferred temperature for copolymerization of [L]-LA and the IPGTC polymerization reaction is 1 30° C., which gave the best the yield, molecular weight, polydispersities and increased efficiency of the incorporation of IPGTC in the polymer. Increasing in the polymerization temperature from 130° C. to 180° C. for $Sn(Oct)_2$-catalyzed copolymerization resulted in increased IPGTC incorporation in the copolymers but decreased Mn. On the basis of copolymer yield and molecular weight, the $Sn(Oct)_2$ catalyst at 130° C. was chosen for more detailed investigations of [L]-LA/IPGTC copolymerization. The temperature at which the polymerization is conducted can be varied to obtain the desired characteristics in the copolymer from the reaction.

3. Modification of [L]-LA/IPGTC Copolymers

The preferred embodiment contains two types of protecting groups, i.e., benzyl protecting groups and ketal protecting groups. The monomer IPGTC was designed with a consideration that different functionalities could be introduced in the [L]-LA/IPGTC copolymer or copolymer I/IPGTC by selectively removing the different protecting groups without a substantial change in molecular weight of the copolymer. The selective deprotection system provides an important and new route to synthesize high molecular weight polyesters with pendant mono-, di-, or tri-hydroxyl groups. By using different reagents, the preferred embodiment allows simple selective removal of the benzyl or ketal, or both groups selectively in the presence of another group. The copolymer having dual types of protected hydroxyl group imparts a unique system for altering the properties of the material formed.

The introduction in copolymers of functional groups such as hydroxyl groups will impart special properties on the copolymer. The vicinal-diol groups in the copolymer provide a variety of opportunities for their use in the development of functional biomedical materials. For example, the hydroxyl groups can be used to attach bioactive molecules for biomedical applications. Alternatively, by controlling the quantity, sites, and distribution of hydroxyl groups in the copolymer, this system provides an unprecedented degree of control over the hydrolytic degradation rate. The hydroxy functional groups can be introduced into the copolymer in ways including but not limited to (1) benzylether deprotection and (2) ketal deprotection.

a. Benzylether deprotection

The preferred method of benzylether deprotection is hydrogenolysis. An array of reagents is known to perform the hydrogenolysis. Hydrogenolysis by far remains the most useful and mild method for removal of the benzyl ether groups. The choice of the deprotecting reagent becomes more important in the presence of other sensitive linkages in the molecule, e.g. ester, ketal, and carbonate linkages. Solvents that do not dissolve the high molecular weight copolymer generally show a slower, or do not allow, debenzylation of the polymer. Preferably, tetrahydrofuran can be a solvent that successfully and completely allows removal of benzyl groups from the [L]-LA/IPGTC copolymer without any substantial loss in the molecular weight. Poly ([L]-LA-co-4.5 mol % IPGTC) ($M_n$=77800, $M_w/M_n$=1.95) was debenzylated using catalytic hydrogenation using Pd/C as catalyst in tetrahydrofuran at room temperature to get the monohydroxy compounds. The basic debenzylation scheme is shown below in Equation 4:

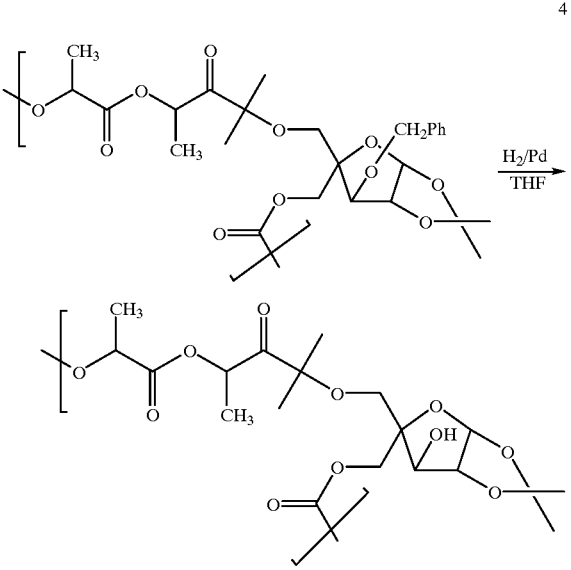

The degree of debenzylation can be monitored and determined by techniques such as $^1$H NMR. FIG. 4 illustrates that the $^1$H NMR pattern can be used to determine the degree of debenzylation. The decrease in the intensity of the signal corresponding to the phenyl group gives the extent that the benzyl groups on the copolymer were removed. Other methods for determining and monitoring benzylether deprotection will be known to a person of ordinary skill in the art.

The copolymer after debenzylation was isolated in quantitative yield as a white solid and the molecular weight was determined by the GPC analysis.

b. Ketal deprotection

The preferred method for the removal of the ketal protecting group of the copolymer or ketal deprotection is by acidic hydrolysis, which can introduce a 1,2 vicinal diol in the copolymer. The resulting copolymers contain ketal groups that can act as intermediates to hydroxyl-containing copolymers. The removal of the ketal protecting group can be accomplished under acidic conditions such as $CF_3COOH/H_2O$ or $BCl_3$ reaction conditions to yield PLA-based copolymers with pendant di-hydroxyl groups. The basic scheme for the removal of the ketal protecting groups from an IPGTC copolymer is shown in Equation 5:

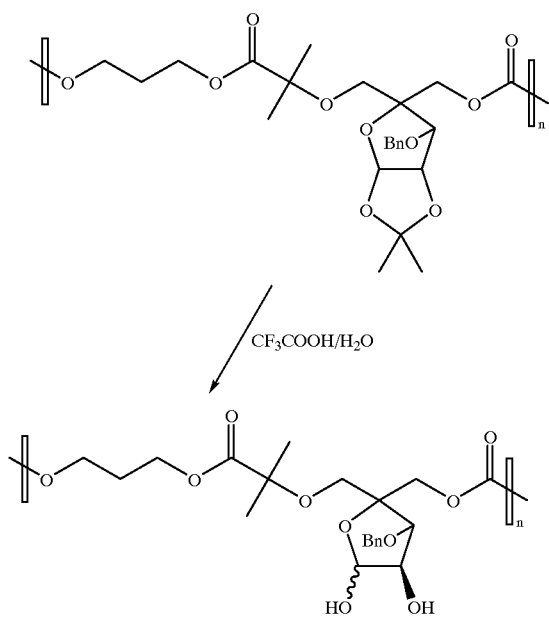

Figure 5:
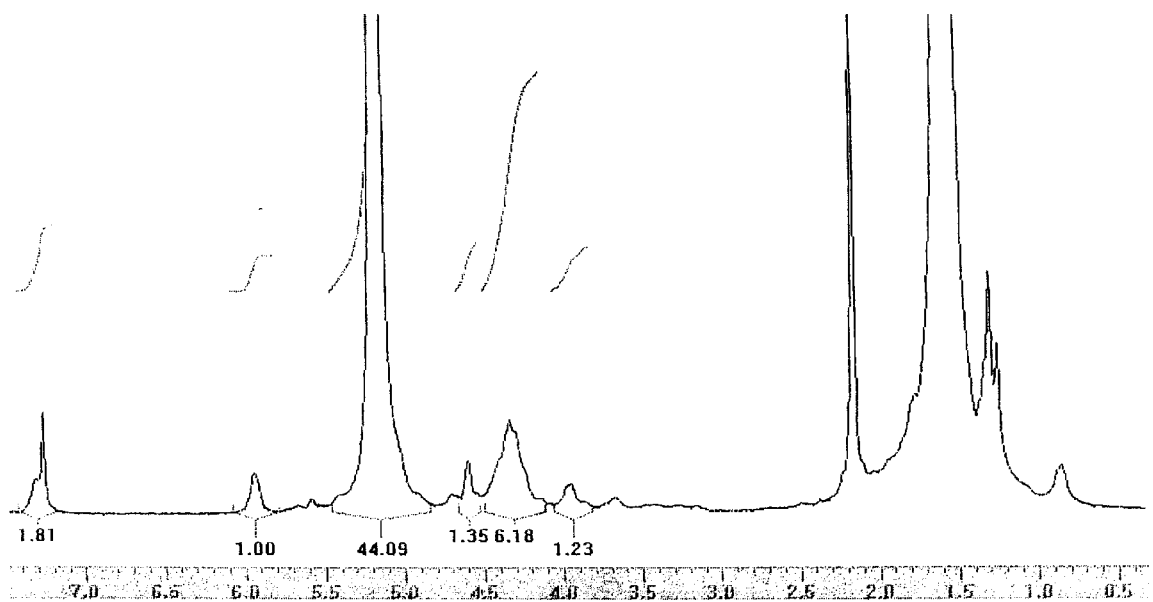
FIG. 5 displays the $^1$H NMR spectrum of debenzylated product which when compared to FIG. 4 demonstrates by the shift in the $^1$H NMR peak that the copolymer has undergone debenzylation.

The ketal protecting group was removed selectively to give the vicinal diol pendant groups. As examples, reactions were conducted using $CF_3COOH/H_2O$ at room temperature. $^1H$ NMR is a method that can be used to determine the mole percent of ketal groups that were converted to vicinal diols (see FIG. 5), in particular by monitoring the intensity of signal at 6.0 ppm because the H-6 protons of repeat units was shifted upfield to 5.50 ppm. For the series of reactions catalyzed by $CF_3COOH/H_2O$, the 100 mole percent removal of ketal protecting groups was achieved in 5 min. However, increasing the time period from 5 to 30 min resulted in a large decrease in the apparent molecular weight of the product.

An advantage of the IPGTC polymers of this invention is that removal of the IPGTC repeat unit ketal protecting groups can be accomplished independently from the benzyl group on the IPGTC comonomer. For example, the IPGTC unit ketal protecting groups were hydrolyzed by using $CF_3COOH/H_2O$ by stirring at room temperature in the presence of benzyl ether groups. Alternatively, the benzyl ether group can be removed using Pd/C as a catalyst in tetrahydrofuran without affecting the ketal groups.

EXAMPLES

The following examples illustrate preparation and processing methods as well as properties of various copolymers of the invention. The following examples are not intended to limit or depart from the scope and spirit of the invention.

The number average molecular weight and molecular weight measurements ($M_n$ and $M_w$, respectively) for these examples were determined by gel permeation chromatography (GPC). GPC analysis was performed using a Waters HPLC system that includes the following: Model 510 pump, Model 717 autosampler, Model 410 refractive index detector (RI) and 500, 103, 104, 105 A° ultrasampler columns in series. Chloroform (HPLC grade) was used as eluent at a flow rate of 1.0 mL/min. The sample concentration and injection volume was 0.2% (wt/wt) and 100 ul, respectively. Molecular weights are determined by using conventional calibration generated with narrow dispersity polystyrene standards (Aldrich chemical company). Viscotec TriSEC (version 3) software was used for data processing.

For the examples herein, Proton $^1H$ NMR were recorded on a Bruker spectrometer at 300 MHz. $^1H$ NMR chemical shifts in parts per million (ppm) are reported downfield from 0.00 ppm using tetramethylsilane (TMS) as an internal reference. The sample concentration used was 4% w/v in chloroform-d. Carbon 13 ($^{13}C$) spectra were recorded at 75.5 MHz on a Bruker spectrometer in 20% w/v chloroform-d solutions. The chemical shifts in ppm were referenced relative to the internal standard chloroform-d at 77.00 ppm.

Example 1

Preparation of Catalysts

The catalyst solution of $Sn(Oct)_2$ was prepared in dry toluene. Stannous octanoate, $Sn(Oct)_2$, was purchased from Aldrich as a liquid and used as received. Toluene and tetrahydrofuran (THF) were dried by distillation from melted sodium. $ZnEt_2$ (1 mL, 1.1 M in toluene) was injected via syringe into a to a previously silanized and flame-dried 10 mL Schlenk tube. The tube was kept under an inert atmosphere. An external ice or acetone bath was used to cool the solution. Once the solution was cooled, 1,4-dioxane solution (99 $\mu$L) containing 9.9 $\mu$L distilled water was slowly added and stirred. After 15 minutes, the cooling bath was removed and the temperature was increased to 25° C. The resulting solution was clear. The solution maintained its catalytic activity up to two (2) weeks stored at about 4° C.

Solutions (1 mol/L) of $Al(O-isopropyl)_3$ were prepared similarly in dry toluene.

Example 2

IPGTC Synthesis

The starting material for IPGTC synthesis is cyclic carbonate of 4-C-hydroxymethyl-1,2-O-(1-methylethylidene)-3-O-(phenylmethyl)-α-D-pentofuranose (HPP). Triethylamine (3.42 g, 0.03387 mol) was added drop wise to a mixture of HPP (5 g, 0.01612 mol) and ethyl chloroformate (3.68 g, 0.03387 mol) dissolved in tetrahydrofuran (THF) (50 ml) at 0° C. over 30 minutes. The reaction mixture was stirred for 2 hours at room temperature and monitored by thin layer chromatography (TLC, EtOAc: petroleum ether; 1:4). After the reaction was complete, the precipitated triethylammonium chloride was filtered out, the filtrate was concentrated to give the end product under reduced pressure. This product was recrystallized from THF and diethylether, and gave the IPGTC monomer in 65% yield. The structure and purity of IPGTC were confirmed by FTIR, $^1$H NMR, $^{13}$C NMR and melting point analysis.

Example 3

Polymerization of IPGTC and [L]-LA

The polymerization ampules (10 ml) were treated with trimethylsilyl chloride, washed with three 5 ml portions of methanol, dried at 100° C. in an oven, and flame dried while purged with dried argon.

The [L]-lactide from Aldrich was purified by twice recrystallization from anhydrous ethyl acetate under a dry nitrogen atmosphere (mp 93–95° C.). Stannous octanoate, Sn(Oct)$_2$, was purchased from Aldrich as a neat liquid and used as received. Toluene and tetrahydrofuran (THF) were dried by distillation from melted sodium. 4-C-hydroxymethyl-1,2-O-(1-methylethylidene)-3-O-(phenylmethyl)-α-D-pentofuranose was prepared according to the procedure described in the literature Sharma et al., *Tetrahedron Letters* 1999, 40, 9145. All other liquid reagents were purchased from Aldrich and were used as received. All liquid reagents were transferred by syringe under a dry argon or nitrogen atmosphere.

Monomers and the catalyst solution were transferred into the ampule under an inert argon atmosphere. The ampule was degassed by several vacuum-purge cycles that also removed solvent introduced in the catalyst solution. The ampule was then sealed under argon and placed in an oil bath for a predetermined reaction time. At the end of the reaction period, the contents of the ampule were dissolved in chloroform (8 ml). The chloroform solution was added to methanol to precipitate the polymer. The precipitate was washed with several portions of methanol, and dried in a vacuum oven (3 mmHg, 40° C., 24 hrs). The yield of copolymer was based on the amount of methanol insoluble copolymer recovered after reactions that were carried out under various conditions.

Example 4

Synthesis of IPGTC-[L]-LA Copolymer with Variable Compositions

This example illustrates that varying the feed ratio affects the copolymer produced. The effects include yield, repeat unit composition, polydispersity (Pd), and number average molecular weight ($M_n$) (see Table 1). A decrease in copolymer percent-yield and $M_n$ values were observed by increasing the IPGTC content in the monomer feed ratio. By decreasing the [L]-LA to IPGTC ration from 91:9 to 64:36, the molar content of IPGTC in the copolymer increased from 4 to 14 percent as shown in entries 2 and 4 of Table 1.

TABLE 1[a]

| Entry | $f_{LA}/f_{IPGTC}$ | Yield | $M_n$ | Pd | $F_{LA}/F_{IPGTC}$ |
|---|---|---|---|---|---|
| 1 | 100/0 | 98% | 83,000 | 2.14 | 100/0 |
| 2 | 91/9 | 78% | 75000 | 2.3 | 96/4 |
| 3 | 73/27 | 74% | 20000 | 1.8 | 94/6.5 |
| 4 | 64/36 | 70% | 13000 | 2.0 | 86/14 |
| 5 | 50/50 | 35% | nd[b] | nd[b] | 79/21 |
| 6 | 0/100[c] | 28% | 7900 | 1.5 | 0/100 |

[a]130° C., Sn (Oct)$_2$ as catalyst, M/I = 200, reaction time: 6 h
[b]Not determined
[c]145° C.

Table 1 illustrates the affect of varying the feed ratios arbitrarily from 100/0 to 0/100. As expected, a feed ratio of 100/0 yielded a polymer that was 100% percent composed of [L]-LA, and a feed ratio of 0/100 yielded a polymer that was 100% IPGTC. $M_n$ varied from 75000 to 20000 when the feed ratio was lowered from 91/9 to 73/27 ([L]-LA/IPGTC). Additionally, the yield decreased as the [L]-LA in the feed ratio was decreased, and specifically the yield decreased by more than 50% when the [L]-LA in the feed ratio was decreased from 64% to 50%. The optimal feed ratio of [L]-LA to IPGTC will depend on the needs of the user. Other reaction parameters at a constant feed ratio can be varied to alter the polymer composition.

Example 5

Effect of Temperature and Copolymer Yield, $M_n$ and Composition

The temperature at which the reaction is conducted affects the yield, $M_n$, polydispersities ($M_n/M_w$) and the content of IPGTC in the polymer. As shown in Table 2 for reactions conducted for 6 hours, the yield can vary by 74% to 43% by a variation in the reaction temperature from 120° C. to 180° C. Moreover, the polydispersity ratio can vary from 2.3 to 1.5 by increasing the temperature from 120° C. to 180° C. The optimal temperature for producing a polymer with the largest $M_n$ is 130° C. and allows the incorporation of 4 percent IPGTC. However, increasing the reaction temperature results in an increase in the IPGTC content of the copolymers.

TABLE 2[a]

| Temperature | Yield (%) | $M_n$ | $M_n/M_w$ | $F_{LA}F_{IPGTC}$ |
|---|---|---|---|---|
| 120 | 74 | 34000 | 2.1 | 98/2 |
| 130 | 78 | 75000 | 2.3 | 96/4 |
| 140 | 70 | 40000 | 2.0 | 94/6 |
| 155 | 60 | 24000 | 2.0 | 9218 |
| 165 | 56 | 15000 | 1.8 | 91/9 |
| 180* | 43 | 9900 | 1.5 | 90/10 |

[a]Sn(Oct)$_2$ as catalyst, M/I = 200, reaction time: 6 h, $f_{LA}/f_{IPGTC}$ = 91:9
*88:12

Example 6

Effect of Reaction Time on Copolymer Yield and $M_n$

Plots of copolymer yield, $M_n$ and monomer conversion versus reaction time are displayed in FIG. 2. The Sn(Oct)$_2$-catalyzed polymerization was carried out at 130° C., M/C=400 and $f_{LA}/f_{IPGTc}$ 91/9. The copolymer yield and Mn increased rapidly to 66% and 56300 in 4 hrs. Further, increase in copolymer yield and was gradual with increased reaction time. By 18 hrs, the copolymer yield and $M_n$ were 77% and 51500 respectively. The conversion of [L]-LA by 6 hr was almost quantitative. In contrast, IPGTC percent-conversion increased slowly to 49% by 18 hrs.

Example 7

Deprotection of the Ketal Group

The deprotection of the ketal group was conducted on the [L]-LA/IPGTC copolymer that contained benzyl ether protecting groups. 0.5 ml of 75% CF$_3$COOH was added to 0.050g of copolymer and the reaction mixture was stirred for a predetermined time at room temperature. The resulting copolymeric product was precipitated by adding water (50 ml). The polymer was separated by filtration, washed with 20 ml of methanol, and dried in a vacuum to constant weight (30–35 mg).

The ketal deprotection of the [L]-LA/IPGTC copolymer occurred within a short period of time without a substantial loss of molecular weight. When the ketal deprotection was completed using 80% $CF_3COOH/H_2O$ at room temperature for 5 minutes, the number average molecular weight of the product showed only a small decrease in value, i.e. 78000 to 66000 Daltons. After 5 minutes, the polydispersity of the resulting product was 1.62. In addition, the mole percent of ketal groups that were converted to hydroxyl groups with the minute reaction time was 40%.

Example 8

Deprotection of Benzyl Group on the IPGTC-[L]-LA Copolymer

The removal of the benzylether protecting group was accomplished by the use of Pd/C in tetrahydrofuran (THF). The deprotection occurred when 0.050 g of 10% Pd/C was added to a solution of 0.100 g of copolymer in 10 ml of anhydrous THF. The air was displaced with hydrogen ($H_2$) and the solution stirred for 16 hrs. The Pd/C was filtered off and carefully washed with THF. The combined filtrate was evaporated to give the debenzylated copolymer as a white solid (0.072 g). This product was dissolved in $CDCl_3$ to acquire the NMR spectral data. By employing the above method for deprotection of benzylether groups of poly ([L]-lactide-co-4.5 mol % IPXTC) of $M_n$=78000, complete deprotection was achieved in 8 hours without a substantial change in the product molecular weight.

The debenzylation of [L]-LA/IPGTC can be conducted under a variety of conditions including variations in the solvents, catalysts, and catalyst concentrations. The use of ethyl acetate and chloroform as solvents resulted in lower degree of debenzylation while requiring a longer time period for the reaction, i.e. 5-6 days for 10% deprotection. Although THF and Pd/H was the optimal for deprotection, results varied as the catalyst concentration was changed.

Example 9

IPGTC Homopolymerization

The homopolymers of IPGTC was obtained using the catalyst $Sn(Oct)_2$ at 145° C. The resulting homopolymer had a number average molecular weight of 7900 Daltons. The physical appearance of the homopolymer was a white solid as was the case with higher molecular weight [L]-LA/IPGTC polymers.

Example 10

Thermal Analysis

The thermal properties of the monomer IPGTC, copolymers from [L]-LA/IPGTC, and [L]-LA/IPGTC copolymers where the IPGTC units were deprotected were analyzed by thermal gravimetric analysis (TGA) and differential scanning calorimetry (DSC). Table 3 presents the results of the TGA thermograms of the different polymers and in particular shows that, based on the onset of decomposition temperature, the thermal stability of poly ([L]-LA-co-4.5 mol % IPGTC) decreased by 40° C. upon the removal of the ketal protecting groups. This deprotection exposed the two hydroxyls of the IPGTC vicinol diol. In contrast, the thermal stability after debenzylation, which left one hydroxyl free per IPGTC unit, was almost unchanged relative to the starting copolymer.

TABLE 3

Decomposition Temperature of Polymers

| No. | Sample | Onset Decomposition Temperature (Celsius) |
| --- | --- | --- |
| 1 | PLA | 251 |
| 2 | Poly(IPGTC) | 278 |
| 3 | Poly([L]-LA-co-4.5 mol % IPGTC) | 222 |
| 4 | Debenzylated Copolymer | 225 |
| 5 | Deketal Copolymer (vicinol diol) | 182 |

Figure 7B:
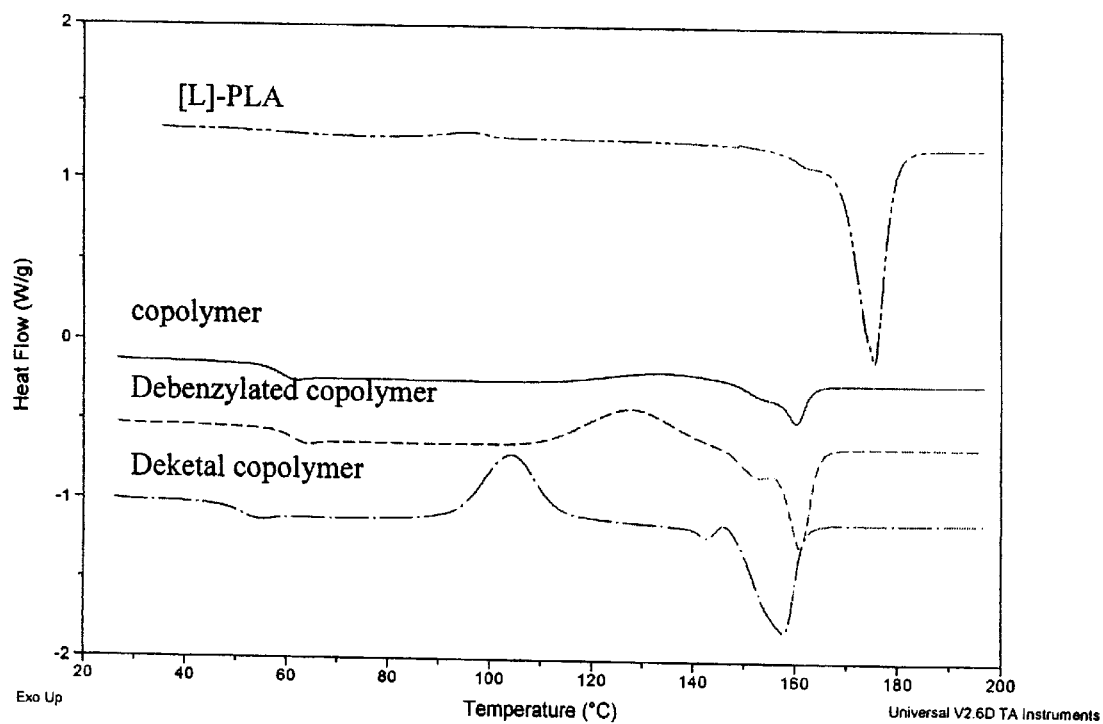
FIG. 7B displays the second heating DSC scans of [L]-LA/IPGTC copolymers before and after benzyl and ketal protecting groups were removed.

The thermal properties were determined by DSC measurement. During the DSC measurements, the precipitated samples were first heated at 10° C./min to 200° C. (first hearting). Subsequently, the sample was cooled from 200° C. to 20° C., and the second heating scan was recorded at a hearting rate of 10° C./min. FIG. 6 shows the first heating DSC scans of [L]-LAIPGTC copolymers as a function of IPGTC content. FIGS. 7A and 7B show the first and second heating DSC scans, respectively, of 1) poly([L]-LA-co-4.5 mol % IPGTC), 2) poly([L]-LA-co-4.5 mol % IPGTC) deprotected by debenzylation to give one free hydroxyl group per IPGTC repeat, and 3) poly([L]-LA-co-4.5 mol % IPGTC) deprotected by hydrolysis of the ketal groups to give two free vicinol hydroxyl groups per IPGTC repeat unit. The first DSC heating scan was used to determine the peak melting temperature ($T_m$) and the corresponding enthalpy of fusion ($\Delta Hf$). The second DSC heating was used to determine the glass transition temperature ($T_g$).

Table 4 presents a summary of the DSC scan results. A comparison of the DSC scans for the [L]-PLA homopolymer and the corresponding [L]-LA/IPGTC copolymers showed that the incorporations of even low levels of IPGTC units caused substantial reductions in the $T_m$ and $\Delta Hf$ values. For example, a comparison of copolymers with 0 and 1 mol % IPGTC units showed that the latter had reductions in $T_m$ by 9° C. (175° C. to 166° C.) and $\Delta Hf$ by 23 J/g (61 J/g to 38 J/g). A further increase in the IPGTC content from 1 to 6 mol % did not significantly alter the $\Delta Hf$ values but did cause a decrease in the $T_m$ from 166° C. to 159° C. No significant change in the $T_g$ values was found by comparison of the [L]-PLA homopolymer and the [L]-LAIPGTC copolymers with up to 6 mol % IPGTC. The homopolymer of IPGTC was successfully prepared, but had a low molecular weight ($M_n$ 7880). A comparison of [L]-PLA and poly(IPGTC) showed that the latter had a higher $T_g$ (69° C. versus 58° C.) but was less crystalline. The $T_m$ and $\Delta Hf$ of poly(IPGTC) are 76° C. and 8 J/g, respectively.

A further analysis of Table 4 shows that deprotection of hydroxyl moieties by either debenzylation or hydrolysis of the ketal groups of IPGTC units did not substantially change the $T_m$ values of the copolymers. However, deprotection of poly([L]-LA-co-4.5 mol % IPGTC) hydroxyl groups did alter the crystallization behavior. The general trend observed is that with deprotection of the IPGTC hydroxyl groups the crystallization kinetics increased. Comparison of poly([L]-LA-co-4.5 mol % IPGTC) with deprotection by debenzylation and hydrolysis of the ketal groups showed that the latter crystallized most rapidly, which may be explained by the lower $T_g$ of the ketal deprotected versus the debenzylated copolymer (52° C. and 58° C., respectively).

TABLE 4

DSC Results of Selected Polymers

| No. | Sample | $M_n$ | $T_m$ (° C.) | $\Delta H_f$(J/g) | $T_g$ (° C.) |
| --- | --- | --- | --- | --- | --- |
| 1 | PLA | 83400 | 175 | 61 | 58 |
| 2 | Poly(IPGTC) | 7880 | 76 | 8 | 69 |
| 3 | [L]-LA-co-1.0 mol % IPGTC | 27400 | 166 | 38 | 52 |
| 4 | [L]-LA-co-1.5 mol % IPGTC | 28300 | 168 | 38 | 54 |
| 5 | [L]-LA-co-2.3 mol % IPGTC | 33500 | 164 | 42 | 55 |
| 6 | [L]-LA-co-4.5 mol % IPGTC | 77800 | 160 | 35 | 59 |
| 7 | [L]-LA-co-6.0 mol % IPGTC | 59900 | 159 | 33 | 56 |
| 8 | Debenzylated [L]-LA-co-4.5 mol % IPGTC | 77400 | 160 | 30 | 58 |
| 9 | Deketal [L]-LA-co-4.5 mol % IPGTC | 66000 | 160 | 38 | 52 |

From the combined information given in Tables 3 and 4, it is concluded that [L]-LA/IPGTC copolymers and the debenzylated copolymer, with at least 4.5 mol % IPGTC units, are suitable for thermal processing in the melt.

Example 11

Copolymerization of IPGTC with ε-Caprolactone

The copolymerization of IPGTC and ε-caprolactone was performed at 90° C. using alternatively $Sn(Oct)_2$ and MAO catalysts as shown below in Equation 6. The polymerizations were carried out for 22 hours and the $f_{IPGTC}/f_{\varepsilon\text{-}Caprolactone}$ feed ratio was 30:70. It was observed that $Sn(Oct)_2$ resulted in low polymer isolated yield with low molecular weight and with MAO the copolymer with 6.5% incorporation of IPGTC in 45% isolated yield was obtained. The number average molecular weight of the copolymer formed was 11,000 with a polydispersity index of 1.46. It is speculated that using zinc and lanthanides catalysts can result in higher polymer yield with a higher molecular weight.

6

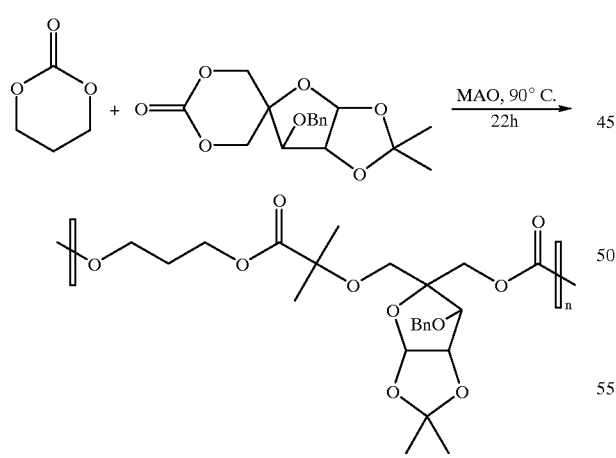

Example 12

Copolymerization of IPGTC with TMC

The copolymerization of IPGTC and TMC was performed at 90° C. using alternatively $Sn(Oct)_2$ and MAO catalysts. Polymerization was carried out for 22 hours and the $f_{IPGTC}/f_{TMC}$ feed ratio was 30:70. It was observed that the MAO as compared to $Sn(Oct)_2$ resulted in relatively higher polymer yields and molecular weights. The polymerization proceeds according to Equation 7. For example, under the above-mentioned conditions with MAO, a 14:86 IPGTC:TMC, copolymer was obtained in 54% isolated yield with $M_n$ 19000 (PD of 1.6). This reaction can be accomplished with zinc-based catalysts as well.

7

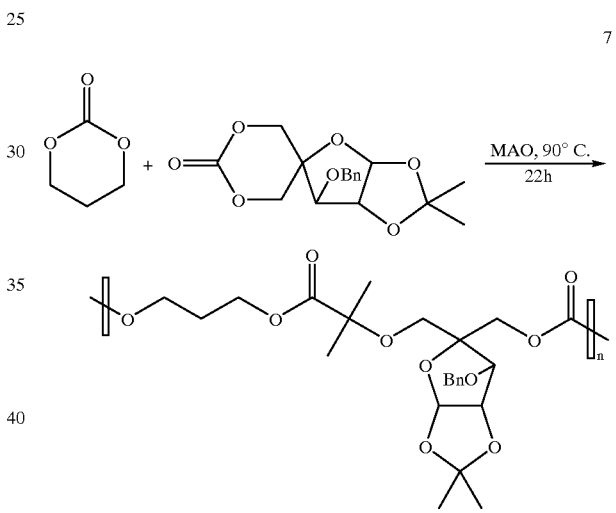

Example 13

Graft copolymer with N-carboxy anhydride

The graft ring-opening polymerization of N-carboxyanhydrides (NCA) was used to introduce peptide side groups. NCA was prepared starting from the γ-monobenzyl ester, which is a derivative of glutamic acid as shown in Equation 8. The monobenzyl glutamic acid (2 g, 0.0084 mole) and triphosgene (840 mg) was dissolved in anhydrous THF. The reaction mixture was stirred for 3 hr at room temperature and the completion of the reaction was monitored by TLC. The NCA product obtained was recrystallized from THF and hexane to get 1.8 g (81% yield).

8

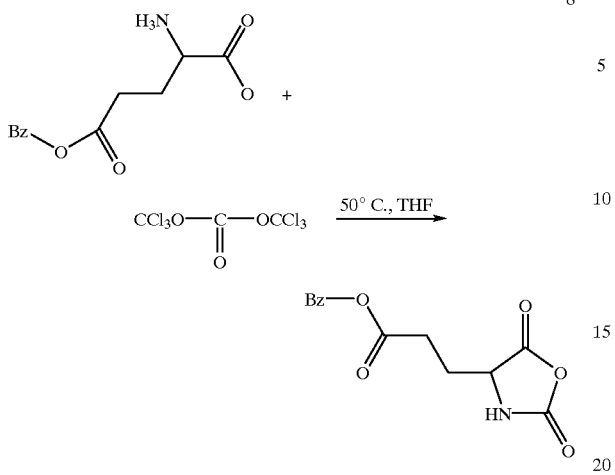

Example 14

NCA Graft Reaction on [L]-LA-co-IPGTC Copolymer

The [L]-LA-co-IPGTC (4.5 mol % IPGTC) and N-carboxy anhydride of monobenzyl glutamic acid were transferred into the polymerization ampule (previously treated with trimethylsilyl chloride and dried) under an inert argon atmosphere. The grafting reaction of NCA on [L]-LA co-IPGTC copolymer is shown in Equation 9. The catalyst solution was added via syringe and the reaction mixture was degassed by several vacuum-purge cycles that also removed solvent introduced in the catalyst solution. The ampule was then sealed under argon and placed in an oil bath maintained at 130° C. for a predetermined time period. At the end of the reaction period the contents of the ampule were dissolved in chloroform. The chloroform solution was added to methanol to precipitate the polymer. The precipitate was washed with several portions of methanol, and dried in a vacuum oven. NMR showed that the NGA graft copolymer was formed.

9

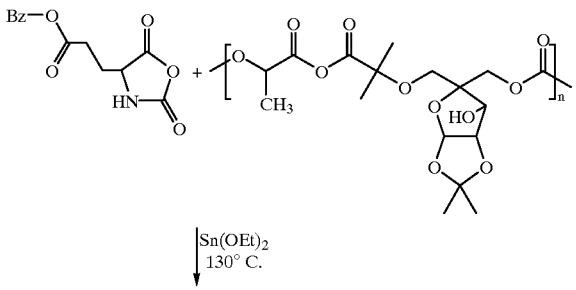

-continued

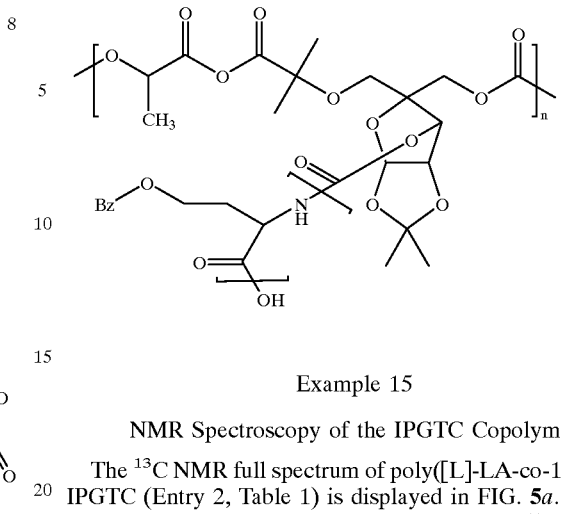

Example 15

NMR Spectroscopy of the IPGTC Copolymer

The $^{13}$C NMR full spectrum of poly([L]-LA-co-15 mol % IPGTC (Entry 2, Table 1) is displayed in FIG. 5a. Assignments of the major resonances were based on (i) the spectrum of the homopolymer [L]-pLA$^{42}$ and (ii) a $^1$H-$^{13}$C correlated 2D NMR (HETCOR) spectrum. Li, et al., *J. Biomater. Sci. Polym. Ed.* 1996, 8(3), 165. The HETCOR spectrum gave cross-peaks between 4.75-1H/85.2-13C, 4.44-1H/72.5-13C, 4.22-1H/82.5-13C and 3.91-1H/71.5-13C ppm. Hence on the basis of above correlations and comparison with the $^{13}$C-NMR of the homopolymer of IPGTC (unpublished results) the $^{13}$C-NMR signals at 137.5, 112.5, 104.5, 85.5, 84.0, 72.5, 71.0, 69.0 27.0, 26.0 and 17.5 were assigned to C7, C13, C8, C6, C4, C2, C5, C11, C9, C10 and C12. Expansions of signals in the carbonyl regions of the spectrum show considerable complexity (FIG. 3b). On the basis of comparison to the homopolymer [L]-PLA, the intense signal at 170.0 ppm was assigned to LLL sequences (L-lactyl unit with directionality —O—CH—(CH3)—CO—). Li, *Biomater. Sci. Polym. Ed.* 1996, 8(3), 165. The neighboring signals, which appear as shoulders of the 170.0 ppm resonance, are likely due to sequence effects beyond triads. For example, these peaks may arise because of IL,LL and LL,LI sequences (I=IPGTC units). Due to the symmetrical nature of the IPGTC as it is formed by the reaction of two primary hydroxyl groups so there is no difference in the directionality along the chain as was the case with IPXTC. Chen, X., Gross, R. A., *Macromolecules* 1999, 32, 308–314.

$^1$H and 13C NMR spectroscopy was used to obtain a structural characterization of the LA/IPGTC polymer. $^1$H and $^{13}$C NMR were used to characterize the [L]-LA/IPGTC copolymers. FIG. 3 displays the $^1$H NMR spectrum of poly([L]-LA-co-15 mol % IPGTC) synthesized by Sn(Oct)$_2$ at 130° C. (Entry 2, Table 1). Comparisons to previously published spectra of [L]-PLA homopolymer showed that the signals at 5.21 and 1.62 ppm are due to [L]-LA repeat unit CH and CH$_3$ protons, respectively. Li, S. M., Espartera, J. L., Foch, P., Vert, M., *J. Biomater. Sci. Polym. Ed.* 1996, 8(3), 165. Signals at 1.30 ppm and 1.45 ppm were assigned to H8/H9 on the basis of the $^1$H NMR spectra of copolymers with different compositions and a $^1$H-$^{13}$C correlated 2D spectrum. The signal at 7.40 ppm was assigned to the phenyl ring present in copolymer. Other assignments were based on observed correlations in the corresponding $^1$H—$^1$H correlation spectroscopy (COSY) NMR spectrum. A cross peak was observed between 5.1 and 1.65 ppm, the former was assigned to CH of [L]-LA units in IPGTC-[L]-LA sequences. Correlations of 5.9 with 4.7 and 4.7 with 4.5 were used to assign signals resulting from protons 6,7 and benzylic group. The benzylic protons are gem coupled and showed signals at both 4.7 and 4.5 each for one proton. The H-5 proton showed no correlations and appeared as singlet at 3.90. Additional correlations of signals at 4.44 with 4.42 and 4.36 with 4.30 showed that signals at 4.44 and 4.42 are due to H2 protons and are gem coupled. Similarly the signals at 4.36 and 4.30 are due to H4 protons and are also gem coupled. Hence the signals were not resolved for the protons of H4/H2 as well as for Hi and benzylic protons. Structural complexity in the $^1$H NMR spectrum of FIG. 3, may be due to diad sequence effects. Thus at the current level of signal resolution and peak assignments, it is difficult to obtain the quantitative data for repeat unit sequence distribution from $^1$H NMR spectra.

NMR spectroscopy was used to confirm the directionality of IPGTC as defined as —O—CX'CX"CH2—O—CO— and —O–CH2—CX"CX'—O—CO—, respectively. The ring opening of symmetrical carbonate leads to unidirectionality in the copolymer sequence, and increases in the IPGTC content of the copolymer. The signals at 169.56 and 169.48 ppm were tentatively assigned to ILL, and LLI, respectively. The ring opening of symmetrical carbonate leads to unidirectionality in the copolymer sequence, and increases in the IPGTC content increases the peak intensity at 154.24.

The above detailed description of the preferred embodiments, examples and the appended figures are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A bioresorbable copolymer comprising products of a reaction between:
   a first comonomer selected from the group consisting of cyclic carbonates, lactones, lactides, lactams, thiolactones, functionalized cyclic carbonates and non-functionalized cyclic carbonates; and
   a second, functionalized, cyclic carbonate comonomer, wherein said second comonomer is a ring structure comprising functional groups.

2. The bioresorbable copolymer composition as characterized in claim 1, wherein the first comonomer is selected from the group consisting of [L]-lactide, [D]-lactide, racemic-lactide, meso-lactide, glycolide, trimethylene carbonate (TMC), dioxanone, ethylene oxide, c-caprolactone, and 1,2-O-isopropylidene-D-xylofuranose-3,5-cyclic carbonate (IPXTC).

3. The bioresorbable copolymer as characterized in claim 2, wherein the second comonomer is IPGTC.

4. The bioresorbable copolymer as characterized in claim 1, wherein said functional groups are protected.

5. The bioresorbable copolymer as characterized in claim 4, wherein said functional groups are hydroxyl groups.

6. The bioresorbable copolymer as characterized in claim 5, wherein said functional groups are hydroxyl groups that are protected by a group selected from the group consisting of benzyl, acetonide (ketal), DMT, benzonide, benzoyl, acetyl, THP (tetrahydropyran), methyl, acrylate, methyl methacrylate, courmaryol, and nucleic acids.

7. The bioresorbable copolymer as characterized in claim 3, wherein said functional group is a pendant group selected from the group consisting of mono-hydroxy, di-hydroxy and tri-hydroxy pendant systems.

8. The bioresorbable copolymer as characterized in claim 7, wherein said pendant groups provide sites to bind biologically active.

9. The bioresorbable copolymer as characterized in claim 8, wherein the biologically active moiety is attached to said pendant group by forces selected from the group comprising of ionic, covalent, hydrophobic, and van der waals forces.

10. The bioresorbable copolymer as characterized in claim 1 arranged in a pattern selected from the group consisting of random, block, alternating, graft, network, and blended copolymers, and mixtures thereof.

11. The bioresorbable copolymer as characterized in claim 3 that is capable of degradation into one or more low toxicity products.

12. The bioresorbable copolymer as characterized in claim 11, wherein the low toxicity products are selected from the group consisting of lactic acid, ethanol, water and carbon dioxide.

13. The bioresorbable copolymer as characterized in claim 3 having a weight average molecular weight between 1000 and 1,000,000 grams per mole.

14. The bioresorbable copolymer as characterized in claim 10 having a graft pattern comprising a main chain of ester and carbonate linkages and having grafts comprising amino acid units.

15. The bioresorbable copolymer as characterized in claim 14 wherein the amino acid units are synthesized by the ring-opening of N-carboxyanhydrides.

16. The bioresorbable copolymer as characterized in claim 2 comprising at least 25 weight percent repeating units derived from a lactide.

17. The bioresorbable copolymer as characterized in claim 2, comprising at least 50 weight percent repeating units derived from a lactide.

18. The bioresorbable copolymer as characterized in claim 3, wherein the IPGTC has the formula:

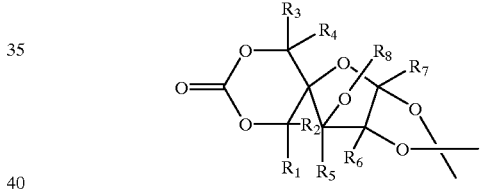

19. The bioresorbable copolymer as characterized in claim 18, wherein $R_1$, $R_2$, $R_3$, $R_4$, $R_5$, $R_6$, $R_7$, and $R_8$ are selected from the group consisting of hydrogen, alkanes, alkenes, alkynes, amine, amide, aromatic rings, alcohols, esters, carboxylic acids, esters, and nitriles.

20. The bioresorbable copolymer as characterized in claim 19, wherein $R_1$, $R_2$, $R_3$, $R_4$, $R_5$, $R_6$, and $R_7$ are hydrogen.

21. The bioresorbable copolymer as characterized in claim 20, wherein the protecting groups are selected from the group consisting of benzyl and ketal.

22. The bioresorbable copolymer as characterized in claim 18, wherein $R_8$ is selected from the group consisting of acrylate, methyl methacrylate, courmaryol, and nucleic acids.

23. The bioresorbable copolymer as characterized in claim 22, wherein $R_8$ is a benzyl moiety.

24. The bioresorbable copolymer as characterized in claim 23, wherein $R_1$, $R_2$, $R_3$, $R_4$, $R_5$, $R_6$, and $R_7$ are hydrogen.

25. A cell scaffold comprising the bioresorbable copolymer as characterized in claim 14, wherein said scaffold supports cell growth.

26. An implantable time-release device comprising the bioresorbable copolymer as characterized in claim 3, wherein the time-release device contains bioactive molecules.

27. An encapsulation device comprising the bioresorbable copolymer as characterized in claim 3, wherein the encapsulation device contains bioactive molecules.

28. A monomer comprising a formula

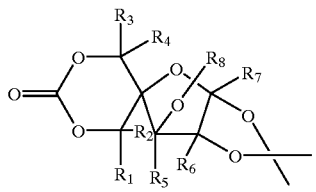

29. The monomer as characterized in claim 28, wherein $R_1$, $R_2$, $R_3$, $R_4$, $R_5$, $R_6$, $R_7$, and $R_8$ are selected from the group consisting of hydrogen, alkanes, alkenes, alkynes, amine, amide, aromatic rings, alcohols, esters, carboxylic acids, esters, and nitriles.

30. The monomer as characterized in claim 29, wherein $R_1$, $R_2$, $R_3$, $R_4$, $R_5$, $R_6$, and $R_7$ are hydrogen.

31. The monomer as characterized in claim 28, wherein $R_8$ is selected from the group consisting of acrylate, methyl methacrylate, courmaryol, and nucleic acids.

32. The monomer as characterized in claim 31, wherein $R_8$ is a benzyl moiety.

33. The monomer as characterized in claim 32, wherein $R_1$, $R_2$, $R_3$, $R_4$, $R_5$, $R_6$, and $R_7$ are hydrogen.

34. A bioresorbable copolymer composition of the formula:

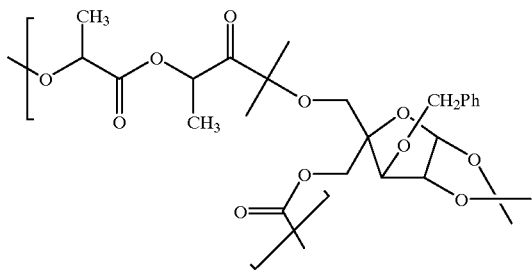

35. A method of preparing 1,2-isopropylidene-3-benzyloxy-glucofuranose-4,4'-cyclic carbonate (IPGTC) comprising the steps of:
 a. preparing a cyclic carbonate of 4-C-hydroxymethyl-1,2-O-(1-methylethylidene)-3-O-(phenylmethyl)-a-D-pentofuranose (H PP);
 b. mixing the HPP with ethylchloroformate dissolved in tetrahydrofuran (THF); and
 c. adding triethylamine to the HPP/ethylchloroformate mixture at low temperature to result in an IPGTC-containing solution.

36. The method of preparing IPGTC as characterized in claim 35, wherein step c is carried out at approximately 0° C.

37. The method of preparing IPGTC as characterized in claim 35, wherein the IPGTC-containing solution is stirred at a temperature of between 30° C. and 40° C.

38. The method of preparing IPGTC as characterized in claim 35, further comprising the step of removing any precipitated triethylamine hydrochloride.

39. The method of preparing IPGTC as characterized in claim 38, further comprising the step of concentrating the IPGTC-containing solution under pressure whereby at least a portion of the IPGTC will recrystallize.

40. A method of preparing a bioresorbable copolymer comprising the steps of:
 a. selecting a first comonomer from the group consisting of cyclic carbonates, lactones, lactides, lactams, thiolactones, functionalized cyclic carbonates and non-functionalized cyclic carbonates;
 b. selecting a second comonomer selected from the group consisting of cyclic carbonate comonomers; and
 c. initiating a copolymerization reaction between said first comonomer and said second comonomer, resulting in the bioresorbable copolymer.

41. The method of preparing a bioresorbable copolymer as characterized in claim 40 under conditions that allow the formation of said bioresorbable copolymer composition.

42. The method of preparing a bioresorbable copolymer as characterized in claim 37, wherein the second comonomer is 1,2-isopropylidene-3-benzyloxy-glucofuranose-4,4'-cyclic carbonate (IPGTC).

43. The method of preparing a bioresorbable copolymer as characterized in claim 42, wherein the IPGTC comprises at least one group selected from the group consisting of alkanes, alkenes, alkynes, protected hydroxyl groups and protected carboxyl groups.

44. The method of preparing a bioresorbable copolymer as characterized in claim 43, wherein the IPGTC comprises at least one protected hydroxyl group and further comprises the step of removing the at least one hydroxyl protecting group subsequent to initiating the copolymerization reaction, thereby introducing at least one hydroxyl group.

45. The method of preparing a bioresorbable copolymer as characterized in claim 43, wherein the IPGTC comprises at least two protected hydroxyl groups and at least one free hydroxyl group.

46. The method of preparing a bioresorbable copolymer as characterized in claim 45, wherein the at least two protected hydroxyl groups are deprotected by removal of the ketal groups.

47. The method of preparing a bioresorbable copolymer as characterized in claim 45, wherein the at least two protected hydroxyl groups are deprotected by hydrolysis of the ketal groups.

48. The method of preparing a bioresorbable copolymer as characterized in claim 43, wherein the IPGTC comprises at least one protected hydroxyl group and at least two free hydroxyl groups.

49. The method of preparing a bioresorbable copolymer as characterized in claim 48, wherein the at least one protected hydroxyl groups is deprotected by removal of the benzyl ether group.

50. The method of preparing a bioresorbable copolymer as characterized in claim 43, wherein the IPGTC comprises at least three protected hydroxyl groups.

51. The method of preparing a bioresorbable copolymer as characterized in claim 50, wherein at least two of the at least three protected hydroxyl groups are selectively deprotected by cleavage of the ketal group.

52. The method of preparing a bioresorbable copolymer as characterized in claim 50, wherein at least one of the at least three protected hydroxyl groups is selectively deprotected by cleavage of the benzyl ether group.

53. The method of preparing a bioresorbable copolymer as characterized in claim 43, wherein the IPGTC comprises at least three protected hydroxyl groups and further comprising the step of introducing a hydroxyl group by means of ketal deprotection subsequent to initiating the copolymerization reaction.

54. The method of preparing a bioresorbable copolymer as characterized in claim 43, wherein the IPGTC comprises at least one protected hydroxyl group and further comprising the step of introducing a hydroxyl group by means of benzyl deprotection subsequent to initiating the copolymerization reaction.

55. The method of preparing a bioresorbable copolymer as characterized in claim 43, wherein the IPGTC comprises at least one protected hydroxyl group and further comprising the step of introducing a hydroxyl group by means of hydrolysis subsequent to initiating the copolymerization reaction.

56. The method of preparing a bioresorbable copolymer as characterized in claim 40, wherein the copolymerization reaction is catalyzed with a catalyst selected from the group consisting of $Sn(Oct)_2$, $ZnEt_2$—$H_2O$, $AlEt_3$, $Al(isobutyl)_3$, $Al(O\text{-secbutyl})_3$, $Al(O\text{-isopropyl})_3$, $La(OR)_3$, and $Y(OR)_3$, wherein R is ethyl, isobutyl, secbutyl, or isopropoxyl.

57. The method of preparing a bioresorbable copolymer as characterized in claim 40, further comprising the step of reacting said bioresorbable composition with a monomer selected from the group consisting of lactones, lactames, thiolactones, cyclic carbonates, and N-carboxy anhydrides to form a graft polymer.

58. The method of preparing a bioresorbable copolymer as characterized in claim 40, wherein said copolymerization reaction is allowed to proceed for between 4 hours and 8 hours.

59. The method of preparing a bioresorbable copolymer as characterized in claim 40, wherein the feed ratio of said first comonomer to said second comonomer is between 90:10 and 99.9:0.1.

60. The method of preparing a bioresorbable copolymer as characterized in claim 59, wherein said copolymerization reaction is allowed to proceed at a temperature of 90° C.

61. The method of preparing a bioresorbable copolymer as characterized in claim 59, wherein said copolymerization reaction is allowed to proceed at a temperature of between 120° C. and 140° C.

* * * * *